(12) United States Patent
Zhan et al.

(10) Patent No.: US 12,065,507 B2
(45) Date of Patent: Aug. 20, 2024

(54) COMPOUNDS AND METHODS FOR USE IN CONNECTION WITH OPIOID USE DISORDERS

(71) Applicant: University of Kentucky Research Foundation, Lexington, KY (US)

(72) Inventors: Chang-Guo Zhan, Lexington, KY (US); Fang Zheng, Lexington, KY (US); Chunhui Zhang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 17/336,165

(22) Filed: Jun. 1, 2021

(65) Prior Publication Data

US 2021/0380721 A1    Dec. 9, 2021

Related U.S. Application Data

(60) Provisional application No. 63/032,995, filed on Jun. 1, 2020.

(51) Int. Cl.
| | |
|---|---|
| *C07K 16/44* | (2006.01) |
| *G01N 33/94* | (2006.01) |
| *G16B 15/30* | (2019.01) |
| *G16B 30/10* | (2019.01) |

(52) U.S. Cl.
CPC ......... *C07K 16/44* (2013.01); *G01N 33/9486* (2013.01); *G16B 15/30* (2019.02); *G16B 30/10* (2019.02); *C07K 2317/24* (2013.01)

(58) Field of Classification Search
CPC .............. C07K 16/44; C07K 2317/24; G01N 33/9486; G16B 15/30; G16B 30/10
See application file for complete search history.

(56) References Cited

U.S. PATENT DOCUMENTS

2004/0175736 A1* 9/2004 Maruyama ........... C07K 16/005
                                                                        435/6.16

FOREIGN PATENT DOCUMENTS

WO    WO-2015106080 A2 *  7/2015    ......... A61K 39/3955

OTHER PUBLICATIONS

Miller III, A.; Glasel, J. A., Comparative Sequence and Immunochemical Analyses of Murine Monoclonal Anti-morphine Antibodies. J. Mol. Biol. 1989, 209, 763-778.
Kussie, P. H.; Anchin, J. M.; Subramaniam, S.; Glasel, J. A.; Linthicum, D. S., Analysis of the binding site architecture of monoclonal antibodies to morphine by using competitive ligand binding and molecular modeling. J. Immunol. 146, 4248-4257.
Sawada, J.-I.; Yamazaki, T.; Terao, T., Molecular and biochemical analyses of combining sites of monoclonal anti-morphine antibodies. Mol. Immunol. 1993, 30, 77-86.
Rahbarizadeh, F.; Rasaee, M. J.; Madani, R.; Rahbarizadeh, M. H.; Omidfar, K., Preparation and Characterization of Specific and High-Affinity Monoclonal Antibodies Against Morphine. Hybridoma 2000, 19, 413-417.
Yang, T. B.; Zhong, P.; Nie, J. L.; Li, J. S.; Qu, L. N.; Li, Y. H.; Kan, G. H., Preparation and Identification of Specific and High-Affinity Monoclonal Antibodies against Morphine. 2002, 21, 197-201.
Matsukizono, M.; Kamegawa, M.; Tanaka, K.; Kohra, S.; Arizono, K.; Hamazoe, Y.; Sugimura, K., Characterization of a Single Chain Fv Antibody that Reacts with Free Morphine. Antibodies 2013, 2, 93-112.
Bogen, I. L.; Boix, F.; Nerem, E.; Mørland, J.; Andersen, J. M., A Monoclonal Antibody Specific for 6-Monoacetylmorphine Reduces Acute Heroin Effects in Mice. J. Pharmacol. Exp. Ther. 2014, 349, 568-576.
Kvello, A. M. S.; Andersen, J. M.; Øiestad, E. L.; Mørland, J.; Bogen, I. L., Pharmacological Effects of a Monoclonal Antibody against 6-Monoacetylmorphine upon Heroin-Induced Locomotor Activity and Pharmacokinetics in Mice. J. Pharmacol. Exp. Ther. 2016, 358, 181-189.
Moghaddam, A.; Borgen, T.; Stacy, J.; Kausmally, L.; Simonsen, B.; Marvik, O. J.; Brekke, O. H.; Braunagel, M., Identification of scFv antibody fragments that specifically recognise the heroin metabolite 6-monoacetylmorphine but hot morphine. J. Immunol. Methods 2003, 280, 139-155.
Pozharski, E.; Wilson, M. A.; Hewagama, A.; Shanafelt, A. B.; Petsko, G.; Ringe, D., Anchoring a Cationic Ligand: The Structure of the Fab Fragment of the Anti-morphine Antibody 9B1 and its Complex with Morphine. Journal of Molecular Biology 2004, 337 (3), 691-697.
Treweek, J. B.; Janda, K. D., An Antidote for Acute Cocaine Toxicity. Mol. Pharm. 2012, 9, 969-978.
Pozharski, E.; Wilson, M. A.; Hewagama, A.; Shanafelt, A. B.; Petsko, G.; Ringe, D., Anchoring a Cationic Ligand: The Structure of the Fab Fragment of the Anti-morphine Antibody 9B1 and its Complex with Morphine. J. Mol. Biol. 2004, 337, 691-697.
Tiller, K. E.; Tessier, P. M., Advances in Antibody Design. Annu. Rev. Biomed. Eng. 2015, 17, 191-216.
Nelson, A. L.; Dhimolea, E.; Reichert, J. M., Development trends for human monoclonal antibody therapeutics. Nature Reviews Drug Discovery 2010, 9 (10), 767-774.

(Continued)

*Primary Examiner* — Julie Ha
*Assistant Examiner* — Erinne R Dabkowski
(74) *Attorney, Agent, or Firm* — Stites & Harbison PLLC; Gary N. Stewart; Mandy Wilson Decker

(57) ABSTRACT

Compositions and methods are provided for use in binding opioids, such as 6-MAM, morphine, heroin, hydrocodone, oxycodone, meperidine, and fentanyl, while avoiding binding to OUD treatment agents, such as naloxone and naltrexone. Methods are also provided for use in a systematic structure-based virtual screening and design approach for identification of such antibodies. Methods are also provided for use in treating OUD. Methods are also provided for use in detecting an opioid in a sample.

12 Claims, 7 Drawing Sheets

Specification includes a Sequence Listing.

(56) References Cited

OTHER PUBLICATIONS

Sawada, et al., Molecular and biochemical analyses of combining sites of monoclonal anti-morphine antibodies. Molecular Immunology 1993, 30 (1), 77-86.

* cited by examiner

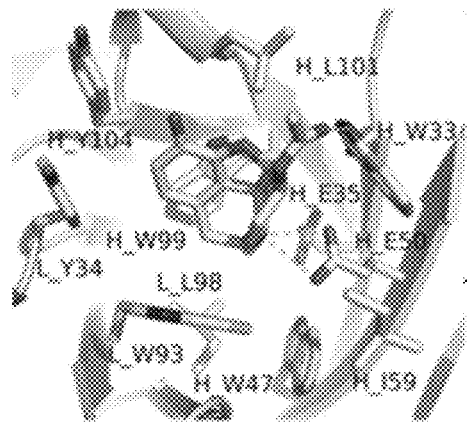 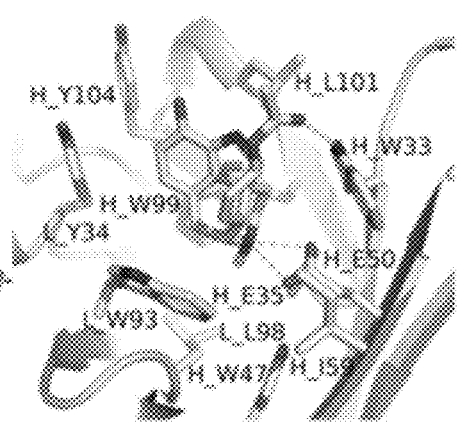
FIG. 3A  FIG. 3B
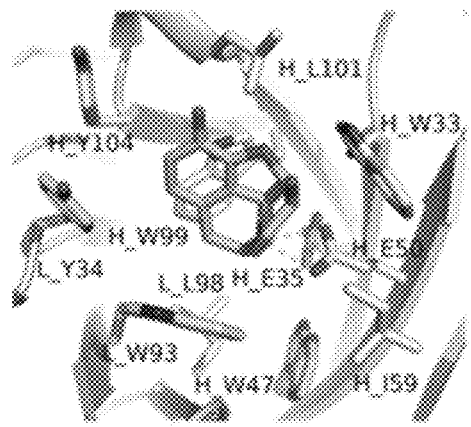 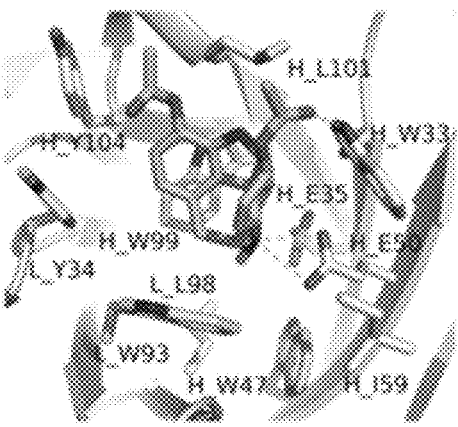
FIG. 3C  FIG. 3D

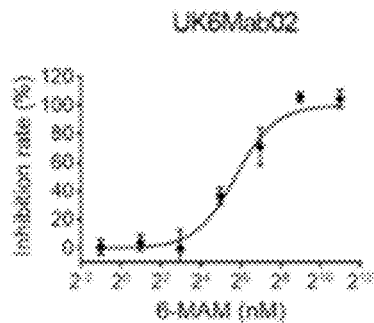 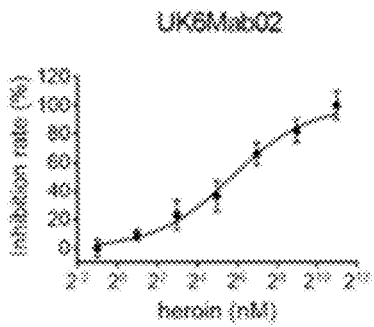 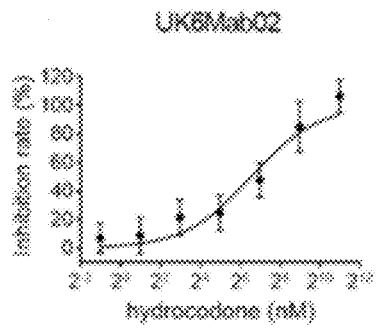
FIG. 5G  FIG. 5H  FIG. 5I
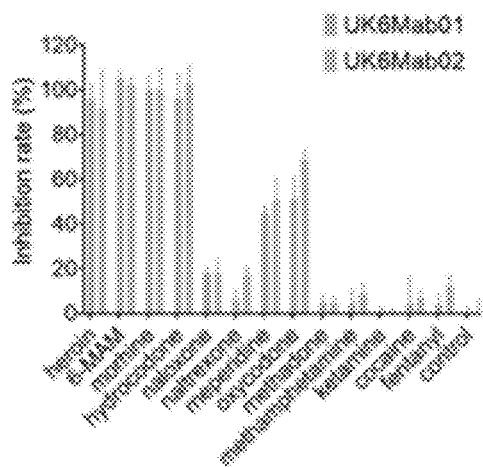 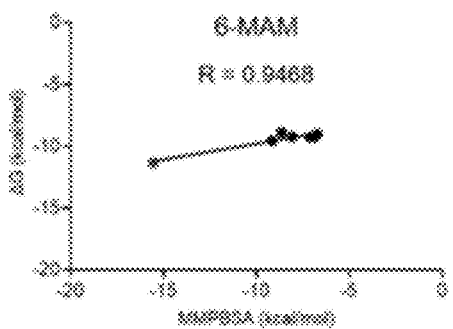
FIG. 5J  FIG. 5K

SEQUENCE LISTING

```
<160> NUMBER OF SEQ ID NOS: 75

<210> SEQ ID NO 1
<211> LENGTH: 119
<212> TYPE: PRT
<213> ORGANISM: Artificial Sequence
<220> FEATURE:
<223> OTHER INFORMATION: Heavy chain

<400> SEQUENCE: 1

Glu Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Asp Thr Ile Phe Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Val Leu Asp Tyr Tyr Gly Met Asp Tyr Trp Gly Gln Gly
```

```
                   100             105              110
Thr Ser Leu Thr Val Ser Ser
             115

<210> SEQ ID NO 2
<211> LENGTH: 98
<212> TYPE: PRT
<213> ORGANISM: Artificial Sequence
<220> FEATURE:
<223> OTHER INFORMATION: IGHV1-69-2*01 Heavy Chain

<400> SEQUENCE: 2

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
                20                  25                  30

Tyr Met His Trp Val Gln Gln Ala Pro Gly Lys Gly Leu Glu Trp Met
            35                  40                  45

Gly Leu Val Asp Pro Glu Asp Gly Glu Thr Ile Tyr Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 3
<211> LENGTH: 98
<212> TYPE: PRT
<213> ORGANISM: Artificial Sequence
<220> FEATURE:
<223> OTHER INFORMATION: IGHV1-46*01 Heavy Chain

<400> SEQUENCE: 3

Gln Val Gln Leu Val Gln Ser Gly Gln Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 4
<211> LENGTH: 15
<212> TYPE: PRT
<213> ORGANISM: Artificial Sequence
<220> FEATURE:
<223> OTHER INFORMATION: IGHJ4*01 Heavy Chain

<400> SEQUENCE: 4

Tyr Phe Asp Tyr Trp Gly Gln Gly Thr Leu Val Thr Val Ser Ser
1               5                   10                  15
```

```
<210> SEQ ID NO 5
<211> LENGTH: 119
<212> TYPE: PRT
<213> ORGANISM: Artificial Sequence
<220> FEATURE:
<223> OTHER INFORMATION: H1 (UK6Mab02) Heavy Chain

<400> SEQUENCE: 5

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Ser Tyr
            20                  25                  30

Trp Ile Glu Trp Val Lys Gln Ala Pro Gly Lys Gly Leu Glu Trp Ile
        35                  40                  45

Gly Glu Ile Asn Pro Ser Gly Gly Ser Thr Ile Tyr Ala Glu Lys Phe
    50                  55                  60

Gln Gly Arg Ala Thr Phe Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Val Leu Asp Tyr Tyr Gly Met Asp Tyr Trp Gly Gln Gly
            100                 105                 110

Thr Ser Leu Thr Val Ser Ser
        115

<210> SEQ ID NO 6
<211> LENGTH: 109
<212> TYPE: PRT
<213> ORGANISM: Artificial Sequence
<220> FEATURE:
<223> OTHER INFORMATION: Light chain

<400> SEQUENCE: 6

Asp Ala Val Val Thr Gln Glu Ser Ala Leu Thr Thr Ser Pro Gly Glu
1               5                   10                  15

Thr Val Ile Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Phe Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Ser Asn Asn
                85                  90                  95

Lys Leu Val Phe Gly Gly Gly Thr Lys Leu Thr Val Leu
            100                 105

<210> SEQ ID NO 7
<211> LENGTH: 98
<212> TYPE: PRT
<213> ORGANISM: Artificial Sequence
<220> FEATURE:
<223> OTHER INFORMATION: IGLV7-46*01 - Light chain

<400> SEQUENCE: 7

Gln Ala Val Val Thr Gln Glu Pro Ser Leu Thr Val Ser Pro Gly Gly
1               5                   10                  15

Thr Val Ile Leu Thr Cys Gly Ser Ser Thr Gly Ala Val Thr Ser Gly
            20                  25                  30
```

```
His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Arg

<210> SEQ ID NO 8
<211> LENGTH: 98
<212> TYPE: PRT
<213> ORGANISM: Artificial Sequence
<220> FEATURE:
<223> OTHER INFORMATION: IGLV8-61*01 - Light chain

<400> SEQUENCE: 8

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile

<210> SEQ ID NO 9
<211> LENGTH: 12
<212> TYPE: PRT
<213> ORGANISM: Artificial Sequence
<220> FEATURE:
<223> OTHER INFORMATION: GLJ3*01 - Light chain

<400> SEQUENCE: 9

Val Val Phe Gly Gly Gly Thr Lys Leu Thr Val Leu
1               5                   10

<210> SEQ ID NO 10
<211> LENGTH: 109
<212> TYPE: PRT
<213> ORGANISM: Artificial Sequence
<220> FEATURE:
<223> OTHER INFORMATION: L1 - Light chain

<400> SEQUENCE: 10

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Ala Asn Trp Val Gln Gln Lys Pro Gly Gln Ala Phe Arg Gly
        35                  40                  45

Leu Ile Gly Ser Thr Asn Thr Arg Ser Ser Gly Val Pro Asp Arg Phe
    50                  55                  60
```

```
Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Lys Leu Val Phe Gly Gly Gly Thr Lys Leu Thr Val Leu
            100                 105

<210> SEQ ID NO 11
<211> LENGTH: 109
<212> TYPE: PRT
<213> ORGANISM: Artificial Sequence
<220> FEATURE:
<223> OTHER INFORMATION: L2 - Light chain

<400> SEQUENCE: 11

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Asp Thr Ser Asn Lys His Ser Trp Thr Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Ala Leu Trp Ser Asn Asn
                85                  90                  95

Lys Leu Val Phe Gly Gly Gly Thr Lys Leu Thr Val Leu
            100                 105

<210> SEQ ID NO 12
<211> LENGTH: 109
<212> TYPE: PRT
<213> ORGANISM: Artificial Sequence
<220> FEATURE:
<223> OTHER INFORMATION: L3 (UK6Mab02) - Light chain

<400> SEQUENCE: 12

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Ala Asn Trp Val Gln Gln Lys Pro Gly Gln Ala Phe Arg Gly
        35                  40                  45

Leu Ile Gly Gly Thr Asn Thr Arg Ser Ser Gly Val Pro Asp Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

Lys Leu Val Phe Gly Gly Gly Thr Lys Leu Thr Val Leu
            100                 105

<210> SEQ ID NO 13
<211> LENGTH: 121
<212> TYPE: PRT
<213> ORGANISM: Artificial Sequence
<220> FEATURE:
<223> OTHER INFORMATION: Ab1 - Heavy chain
```

```
<220> FEATURE:
<221> NAME/KEY: misc_feature
<222> LOCATION: (10)..(10)
<223> OTHER INFORMATION: Xaa can be any naturally occurring amino acid

<400> SEQUENCE: 13
```

| | | | | | | | | | | | | | | | |
|---|---|---|---|---|---|---|---|---|---|---|---|---|---|---|---|
| Gln | Val | Gln | Leu | Gln | Gln | Ser | Gly | Pro | Xaa | Leu | Met | Glu | Pro | Gly | Ala |
| 1 | | | | 5 | | | | | 10 | | | | | 15 | |
| Ser | Val | Lys | Ile | Ser | Cys | Arg | Ala | Ser | Gly | Tyr | Thr | Phe | Arg | Thr | Tyr |
| | | | 20 | | | | | 25 | | | | | 30 | | |
| Trp | Ile | Glu | Trp | Ile | Arg | Glu | Arg | Pro | Gly | His | Gly | Leu | Glu | Trp | Ile |
| | | | 35 | | | | | 40 | | | | | 45 | | |
| Gly | Glu | Ile | Leu | Pro | Gly | Ser | Gly | Phe | Thr | Lys | Tyr | Asn | Glu | Lys | Phe |
| | 50 | | | | | 55 | | | | | 60 | | | | |
| Thr | Gly | Lys | Ala | Thr | Ile | Thr | Ala | Glu | Ala | Ser | Ser | Asn | Thr | Ala | Tyr |
| 65 | | | | | 70 | | | | | 75 | | | | | 80 |
| Val | Gln | Leu | Asn | Ser | Leu | Thr | Ser | Glu | Asp | Ser | Ala | Val | Tyr | Tyr | Cys |
| | | | | 85 | | | | | 90 | | | | | 95 | |
| Thr | Arg | Trp | Gly | Thr | Gly | Ala | Gly | Ile | Ile | Val | Met | Asp | Phe | Trp | Gly |
| | | | 100 | | | | | 105 | | | | | 110 | | |
| Arg | Gly | Thr | Ser | Val | Thr | Val | Ser | Ser | | | | | | | |
| | | | 115 | | | | | 120 | | | | | | | |

```
<210> SEQ ID NO 14
<211> LENGTH: 120
<212> TYPE: PRT
<213> ORGANISM: Artificial Sequence
<220> FEATURE:
<223> OTHER INFORMATION: Ab2 - Heavy chain
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 14
```

| | | | | | | | | | | | | | | | |
|---|---|---|---|---|---|---|---|---|---|---|---|---|---|---|---|
| Gln | Val | Gln | Leu | Gln | Gln | Pro | Gly | Xaa | Glu | Leu | Val | Lys | Pro | Gly | Xaa |
| 1 | | | | 5 | | | | | 10 | | | | | 15 | |
| Ser | Val | Arg | Leu | Ser | Cys | Lys | Ala | Thr | Gly | Tyr | Thr | Phe | Ala | Thr | Tyr |
| | | | 20 | | | | | 25 | | | | | 30 | | |
| Trp | Met | Asn | Trp | Val | Lys | Gln | Arg | Pro | Gly | Gln | Gly | Leu | Glu | Trp | Ile |
| | | | 35 | | | | | 40 | | | | | 45 | | |
| Gly | Glu | Ile | Asn | Pro | Ser | Asn | Gly | Arg | Thr | Asn | Tyr | Asn | Glu | Arg | Phe |
| | 50 | | | | | 55 | | | | | 60 | | | | |
| Gln | Asn | Lys | Ala | Ser | Leu | Thr | Val | Asp | Lys | Ser | Ser | Ser | Thr | Ala | Tyr |
| 65 | | | | | 70 | | | | | 75 | | | | | 80 |
| Met | Gln | Leu | Thr | Ser | Leu | Thr | Ser | Glu | Asp | Ser | Ala | Val | Tyr | Phe | Cys |
| | | | | 85 | | | | | 90 | | | | | 95 | |
| Ala | Arg | Trp | Val | Leu | Arg | Pro | Leu | Tyr | Ala | Leu | Asp | Tyr | Trp | Gly | Gln |
| | | | 100 | | | | | 105 | | | | | 110 | | |
| Gly | Thr | Ser | Val | Thr | Val | Ser | Ser | | | | | | | | |
| | | | 115 | | | | | 120 | | | | | | | |

```
<210> SEQ ID NO 15
<211> LENGTH: 120
<212> TYPE: PRT
<213> ORGANISM: Artificial Sequence
<220> FEATURE:
```

```
<223> OTHER INFORMATION: Ab3 - Heavy chain
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid

<400> SEQUENCE: 15

Gln Val Gln Leu Gln Gln Pro Gly Xaa Glu Leu Val Lys Pro Gly Xaa
1               5                   10                  15

Ser Val Arg Leu Ser Cys Lys Ala Thr Gly Tyr Thr Phe Ala Thr Tyr
            20                  25                  30

Trp Met Asn Trp Val Lys Xaa Arg Pro Gly Gln Gly Leu Glu Trp Ile
        35                  40                  45

Gly Glu Ile Asn Pro Ser Asp Gly Arg Thr Asn Tyr Asn Asp Arg Phe
    50                  55                  60

Lys Asn Lys Ala Thr Leu Thr Val Asp Ile Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Val Leu Arg Pro Leu Tyr Ala Leu Asp Tyr Trp Gly Gln
            100                 105                 110

Gly Thr Ser Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: Ab4 - Heavy chain
<220> FEATURE:
<221> NAME/KEY: misc_feature
<222> LOCATION: (115)..(115)
<223> OTHER INFORMATION: Xaa can be any naturally occurring amino acid

<400> SEQUENCE: 16

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Val Met Ser Trp Val Arg Gln Thr Pro Glu Lys Arg Leu Glu Trp Val
        35                  40                  45

Ala Ser Ile Ser Gly Gly Gly Thr Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Ala Ala Met Phe Tyr Cys Ala
                85                  90                  95

Arg Glu Asp Tyr Tyr Gly Ser Ser Tyr Trp Tyr Phe Asp Val Trp Gly
            100                 105                 110

Ala Gly Xaa Thr Val Thr Val Ser Ser
        115                 120
```

```
<210> SEQ ID NO 17
<211> LENGTH: 121
<212> TYPE: PRT
<213> ORGANISM: Artificial Sequence
<220> FEATURE:
<223> OTHER INFORMATION: Ab5 - Heavy chain
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid

<400> SEQUENCE: 17

Glu Val Lys Leu Val Glu Ser Gly Xaa Gly Xaa Val Lys Pro Gly Gly
 1               5                  10                  15

Ser Leu Lys Leu Ser Cys Ala Ala Ser Gly Phe Thr Phe Ser Lys Tyr
            20                  25                  30

Val Met Ser Trp Val Arg Gln Thr Pro Glu Arg Arg Leu Glu Trp Val
        35                  40                  45

Ala Ser Ile Gly Val Ser Gly Ile Thr Tyr Phe Pro Asp Ser Val Lys
    50                  55                  60

Gly Arg Phe Thr Ile Ser Arg Asp Asn Gly Arg Asn Val Leu Tyr Leu
65                  70                  75                  80

Gln Met Ser Ser Leu Arg Ser Glu Asp Thr Ala Met Tyr Tyr Cys Ala
                85                  90                  95

Arg Glu Asp Tyr Tyr Gly Ser Arg Tyr Trp Tyr Phe Asp Val Trp Gly
            100                 105                 110

Ala Gly Thr Xaa Val Thr Val Ser Ser
        115                 120

<210> SEQ ID NO 18
<211> LENGTH: 121
<212> TYPE: PRT
<213> ORGANISM: Artificial Sequence
<220> FEATURE:
<223> OTHER INFORMATION: Ab6 - Heavy chain
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid

<400> SEQUENCE: 18

Glu Val Lys Leu Val Glu Ser Gly Xaa Xaa Xaa Val Lys Pro Gly Gly
 1               5                  10                  15

Ser Leu Lys Leu Ser Cys Ala Ala Ser Gly Phe Ser Phe Ser Arg Tyr
            20                  25                  30

Val Leu Ser Trp Val Arg Gln Thr Pro Glu Lys Arg Leu Glu Trp Val
        35                  40                  45

Ala Ser Ile Ser Ser Gly Gly Thr Thr Tyr Phe Pro Asp Ser Val Lys
    50                  55                  60

Gly Arg Phe Thr Ile Ser Arg Asp Ile Ala Arg Asn Ile Leu Tyr Leu
65                  70                  75                  80

Gln Leu Ser Ser Leu Arg Ser Asp Asp Thr Ala Met Tyr Tyr Cys Ala
```

```
                    85                  90                  95

Arg Glu Asp Tyr Tyr Gly Gly Arg Tyr Trp Tyr Phe Asp Val Trp Gly
            100                 105                 110

Ala Gly Xaa Thr Val Thr Val Ser Ser
        115                 120

<210> SEQ ID NO 19
<211> LENGTH: 121
<212> TYPE: PRT
<213> ORGANISM: Artificial Sequence
<220> FEATURE:
<223> OTHER INFORMATION: Ab7 - Heavy chain

<400> SEQUENCE: 19

Glu Val Lys Leu Val Glu Ser Gly Ala Gly Val Val Lys Pro Gly Gly
1               5                   10                  15

Ser Leu Lys Leu Ser Cys Glu Ala Ser Gly Phe Ser Phe Ser Arg Tyr
                20                  25                  30

Val Met Ser Trp Val Arg Gln Thr Pro Glu Lys Arg Leu Glu Trp Val
            35                  40                  45

Ala Ser Ile Ser Ser Gly Gly Arg Thr Tyr Tyr Pro Gly Ser Glu Met
50                  55                  60

Gly Arg Phe Thr Ile Ser Arg Asp Ser Ala Arg Asn Ile Leu Tyr Leu
65                  70                  75                  80

Gln Met Ser Ser Leu Lys Ser Glu Asp Thr Ala Met Phe Tyr Cys Ala
                85                  90                  95

Arg Glu Asp Tyr Tyr Gly Gly Arg Tyr Trp Tyr Phe Asp Val Trp Gly
            100                 105                 110

Ala Gly Thr Thr Val Thr Val Ser Ser
        115                 120

<210> SEQ ID NO 20
<211> LENGTH: 123
<212> TYPE: PRT
<213> ORGANISM: Artificial Sequence
<220> FEATURE:
<223> OTHER INFORMATION: Ab8 - Heavy chain
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid

<400> SEQUENCE: 20

Glu Val Ile Cys Leu Val Glu Ser Gly Xaa Gly Val Val Ile Cys Pro
1               5                   10                  15

Gly Gly Ser Leu Lys Leu Ser Cys Ala Ala Ser Gly Phe Ser Phe Ser
                20                  25                  30

Arg Tyr Val Met Ser Trp Val Arg Gln Thr Pro Glu Lys Arg Leu Glu
            35                  40                  45

Trp Val Ala Ser Ile Ser Ser Gly Gly Arg Thr Tyr Tyr Pro Gly Ser
50                  55                  60

Glu Thr Gly Arg Phe Thr Ile Ser Arg Asp Ser Ala Arg Asn Ile Leu
65                  70                  75                  80
```

Tyr Leu Gln Met Ser Ser Leu Arg Ser Glu Asp Thr Ala Ile Phe Tyr
                85                  90                  95

Cys Ala Arg Glu Asp Tyr Tyr Gly Gly Arg Tyr Trp Tyr Phe Asp Val
            100                 105                 110

Trp Gly Xaa Gly Thr Xaa Val Thr Val Ser Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: Ab9 - Heavy chain
<220> FEATURE:
<221> NAME/KEY: misc_feature
<222> LOCATION: (9)..(11)
<223> OTHER INFORMATION: Xaa can be any naturally occurring amino acid

<400> SEQUENCE: 21

Glu Val Lys Leu Val Glu Ser Gly Xaa Xaa Xaa Val Lys Pro Gly Gly
1               5                   10                  15

Ser Leu Lys Leu Ser Cys Ala Ala Ser Gly Phe Ser Phe Ser Asp Tyr
                20                  25                  30

Val Met Ser Trp Val Arg Gln Thr Pro Glu Lys Arg Leu Glu Trp Val
            35                  40                  45

Ala Ser Ile Ser Ser Gly Gly Arg Thr Tyr Tyr Pro Gly Ser Val Lys
        50                  55                  60

Gly Arg Phe Thr Ile Ser Arg Asp Asp Arg Asn Ile Leu Tyr Leu
65                  70                  75                  80

Gln Met Asn Ser Leu Arg Ser Glu Asp Thr Ala Met Phe Tyr Cys Ala
                85                  90                  95

Arg Glu Asp Tyr Tyr Asp Ser Ser Tyr Trp Tyr Phe Asp Val Trp Gly
            100                 105                 110

Thr Gly Thr Thr Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: Ab10 - Heavy chain
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid

<400> SEQUENCE: 22

Gln Val Gln Leu Gln Gln Ser Gly Pro Xaa Leu Met Lys Pro Gly Xaa
1               5                   10                  15

Ser Val Lys Ile Ser Cys Lys Ala Thr Gly Tyr Thr Phe Arg Thr Tyr
                20                  25                  30

Trp Ile Glu Trp Ile Ile Cys Glu Arg Pro Gly His Gly Leu Glu Trp
            35                  40                  45

Ile Gly Glu Ile Leu Pro Gly Ser Gly Ile Thr Lys Tyr Xaa Glu Lys

Phe Lys Gly Lys Ala Ile Ile Thr Ala Asp Thr Ser Ser Asn Thr Ala
65                  70                  75                  80

Tyr Val Gln Leu Ser Ser Leu Thr Ser Glu Asp Ser Ala Val Tyr Tyr
                85                  90                  95

Cys Thr Arg Trp Gly Thr Gly Thr Gly His Val Met Asp Tyr Trp Gly
            100                 105                 110

Gln Gly Thr Ser Val Thr Val Ser Ser
        115                 120

<210> SEQ ID NO 23
<211> LENGTH: 127
<212> TYPE: PRT
<213> ORGANISM: Artificial Sequence
<220> FEATURE:
<223> OTHER INFORMATION: Ab11 - Heavy chain

<400> SEQUENCE: 23

Glu Val Asn Leu Leu Glu Ser Gly Gly Gly Leu Val Gln Pro Gly Gly
1               5                   10                  15

Ser Leu Lys Val Ser Cys Ala Ala Ser Gly Phe Asp Phe Ser Arg Phe
            20                  25                  30

Trp Met Ser Trp Val Arg Gln Ala Pro Gly Lys Gly Leu Glu Trp Ile
        35                  40                  45

Gly Glu Ile Asn Pro Ser Ser Asn Thr Ile Asn Tyr Thr Pro Ser Leu
    50                  55                  60

Ile Cys Glu Arg Phe Ile Ile Ser Arg Asp Asn Ala Ile Cys Asn Thr
65                  70                  75                  80

Leu Tyr Leu Gln Met Ser Lys Val Arg Pro Glu Asp Thr Gly Leu Tyr
                85                  90                  95

Tyr Cys Ala Met Thr Lys Ser Val Tyr Asn Tyr Gly Ser His Tyr Tyr
            100                 105                 110

Tyr Phe Asp Val Trp Gly Ala Gly Thr Thr Val Thr Val Ser Ser
        115                 120                 125

<210> SEQ ID NO 24
<211> LENGTH: 120
<212> TYPE: PRT
<213> ORGANISM: Artificial Sequence
<220> FEATURE:
<223> OTHER INFORMATION: Ab12 - Heavy chain

<400> SEQUENCE: 24

Gln Val His Leu Gln Gln Ser Gly Ala Glu Leu Met Lys Pro Gly Ser
1               5                   10                  15

Ser Val Lys Ile Ser Cys Lys Thr Thr Gly Tyr Thr Phe Ser Asn Tyr
            20                  25                  30

Trp Ile Glu Trp Ile Lys Glu Arg Pro Gly His Gly Leu Val Trp Ile
        35                  40                  45

Gly Glu Ile Leu Pro Gly Thr Gly Arg Thr Phe Tyr Ser Glu Asn Phe
    50                  55                  60

Lys Val Ile Cys Ala Thr Phe Ile Thr Asp Thr Ser Ser Asn Thr Ala
65                  70                  75                  80

Tyr Leu Gln Leu Ser Ser Leu Thr Ser Glu Asp Ser Ala Val Tyr Tyr
                85                  90                  95

Cys Ala Arg Trp Phe Arg Asp Leu Tyr Gly Val Asp Tyr Trp Gly Gln
            100                 105                 110

-continued

```
Gly Thr Ser Val Thr Val Ser Ser
        115                 120

<210> SEQ ID NO 25
<211> LENGTH: 123
<212> TYPE: PRT
<213> ORGANISM: Artificial Sequence
<220> FEATURE:
<223> OTHER INFORMATION: Ab13 - Heavy chain

<400> SEQUENCE: 25

Glu Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Phe Thr Pro Gly Ile Thr Gly Leu Glu
        35                  40                  45

Trp Ile Gly Glu Ile Leu Pro Gly Ser Gly Asp Thr Ile Phe Asn Glu
    50                  55                  60

Ile Cys Phe Lys Gly Ile Cys Ala Thr Phe Thr Ala Asp Thr Ser Ser
65                  70                  75                  80

Asn Thr Ala Tyr Met Gln Leu Ser Ser Leu Thr Ser Glu Asp Ser Ala
                85                  90                  95

Val Tyr Tyr Cys Ala Arg Trp Val Leu Asp Tyr Tyr Gly Met Asp Tyr
            100                 105                 110

Trp Gly Gln Gly Thr Ser Leu Thr Val Ser Ser
        115                 120

<210> SEQ ID NO 26
<211> LENGTH: 138
<212> TYPE: PRT
<213> ORGANISM: Artificial Sequence
<220> FEATURE:
<223> OTHER INFORMATION: Ab14 - Heavy chain

<400> SEQUENCE: 26

Met Asp Phe Gly Leu Ile Phe Phe Ile Val Ala Leu Leu Lys Gly Val
1               5                   10                  15

Gln Cys Glu Val Ile Cys Leu Leu Glu Ser Gly Gly Gly Leu Val Gln
            20                  25                  30

Pro Gly Gly Ser Leu Lys Leu Ser Cys Ala Ala Ser Gly Phe Asp Phe
        35                  40                  45

Ser Arg Tyr Trp Ile Leu Val Arg Gln Ala Pro Gly Lys Gly Leu Glu
    50                  55                  60

Trp Ile Gly Glu Ile Asn Pro Ile Ser Thr Thr Ile Phe Tyr Thr
65                  70                  75                  80

Pro Ser Leu Met Asp Lys Phe Ile Ile Ser Arg Asp Asn Ala Lys Asn
                85                  90                  95

Thr Leu Tyr Leu Gln Met Thr Lys Val Arg Ser Glu Asp Thr Ala Leu
            100                 105                 110

Tyr Tyr Cys Ala Arg Trp Gly Asp Lys Tyr Leu Phe Asp Phe Ile Trp
        115                 120                 125

Gly Gln Gly Thr Thr Leu Thr Val Ser Ser
    130                 135

<210> SEQ ID NO 27
<211> LENGTH: 124
<212> TYPE: PRT
<213> ORGANISM: Artificial Sequence
```

<220> FEATURE:
<223> OTHER INFORMATION: Ab15 - Heavy chain

<400> SEQUENCE: 27

Glu Val Ile Cys Pro Leu Glu Ser Gly Gly Gly Leu Val Gln Pro Gly
1               5                   10                  15

Gly Ser Leu Ile Cys Leu Ser Cys Ala Ala Ser Gly Phe Asp Phe Ser
            20                  25                  30

Arg Tyr Trp Met Ser Trp Val Arg Gln Ala Pro Gly Lys Gly Leu Glu
        35                  40                  45

Trp Ile Gly Glu Ile His Pro Asp Ser Ser Thr Ile Phe Tyr Thr Pro
    50                  55                  60

Ser Leu Ile Cys Asp Ile Cys Phe Ile Ile Ser Arg Asp Asn Ala Ile
65                  70                  75                  80

Cys Glu Thr Leu Tyr Leu Gln Met Thr Lys Val Arg Ser Glu Asp Thr
                85                  90                  95

Ala Leu Tyr Phe Cys Ala Arg Trp Ser Leu Arg Gly Tyr Tyr Phe Asp
            100                 105                 110

Tyr Trp Gly Gln Gly Thr Thr Leu Thr Val Ser Ser
        115                 120

<210> SEQ ID NO 28
<211> LENGTH: 122
<212> TYPE: PRT
<213> ORGANISM: Artificial Sequence
<220> FEATURE:
<223> OTHER INFORMATION: Ab16 - Heavy chain

<400> SEQUENCE: 28

Glu Val Lys Pro Leu Glu Ser Gly Gly Gly Leu Val Gln Pro Cys Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Arg Lys Arg Leu Glu Trp Ile
        35                  40                  45

Gly Glu Ile Asn Pro Asp Ser Ser Thr Ile Thr Tyr Thr Pro Ser Leu
    50                  55                  60

Ile Cys Asp Ile Cys Phe Ile Ile Ser Arg Asp Asn Ala Lys Asn Thr
65                  70                  75                  80

Leu Tyr Leu Gln Met Ser Lys Val Arg Ser Glu Asp Thr Ala Leu Tyr
                85                  90                  95

Tyr Cys Ala Ser Trp Tyr Gly Leu Arg Leu Ser Tyr Phe Asp Val Trp
            100                 105                 110

Gly Ala Gly Thr Thr Val Thr Val Ser Ser
        115                 120

<210> SEQ ID NO 29
<211> LENGTH: 125
<212> TYPE: PRT
<213> ORGANISM: Artificial Sequence
<220> FEATURE:
<223> OTHER INFORMATION: Ab17 - Heavy chain

<400> SEQUENCE: 29

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp Tyr
            20                  25                  30

Ala Ile His Met Val Arg Gln Ala Pro Gly Lys Gly Leu Glu Trp Val
            35                  40                  45

Ser Gly Ile Ser Trp Asp Ser Tyr Thr Thr Gly Tyr Ala Asp Ser Val
 50                  55                  60

Lys Gly Arg Phe Thr Val Ser Arg Asp Asn Ala Lys Asn Ser Leu Tyr
65                  70                  75                  80

Leu Gln Met Asn Ser Leu Arg Pro Glu Asp Thr Ala Val Tyr Tyr Cys
                85                  90                  95

Ala Lys Ala Pro Ser Pro Arg Val Ile Ile Glu Tyr Phe Asp Ser
            100                 105                 110

Asp Tyr Trp Gly Gln Gly Thr Ser Leu Thr Val Ser Ser
        115                 120                 125

<210> SEQ ID NO 30
<211> LENGTH: 126
<212> TYPE: PRT
<213> ORGANISM: Artificial Sequence
<220> FEATURE:
<223> OTHER INFORMATION: Ab18 - Heavy chain

<400> SEQUENCE: 30

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp Tyr
            20                  25                  30

Ala Ile His Met Val Arg Gln Ala Pro Gly Lys Gly Leu Glu Trp Val
            35                  40                  45

Ser Gly Ile Ser Trp Asp Ser Tyr Thr Thr Gly Tyr Ala Asp Ser Val
 50                  55                  60

Lys Gly Arg Phe Thr Val Ser Arg Asp Asn Ala Ile Cys Asn Ser Leu
65                  70                  75                  80

Tyr Leu Gln Met Asn Ser Leu Arg Pro Glu Asp Thr Ala Val Tyr Tyr
                85                  90                  95

Cys Ala Lys Ala Pro Ser Pro Arg Arg Val Ile Ile Glu Tyr Phe Asp
            100                 105                 110

Ser Asp Tyr Trp Gly Gln Gly Thr Ser Leu Thr Val Ser Ser
        115                 120                 125

<210> SEQ ID NO 31
<211> LENGTH: 125
<212> TYPE: PRT
<213> ORGANISM: Artificial Sequence
<220> FEATURE:
<223> OTHER INFORMATION: Ab19 - Heavy chain

<400> SEQUENCE: 31

Glu Val Gln Leu Val Glu Ser Gly Gly Gly Leu Val Gln Pro Gly Arg
1               5                   10                  15

Ser Leu Arg Leu Ser Cys Ala Ser Gly Phe Ser Phe Gly Asp Tyr
            20                  25                  30

Ala Arg Ile Met Val Arg Gln Ala Pro Gly Lys Gly Leu Glu Trp Val
            35                  40                  45

Ser Gly Ile Ser Trp Asp Ser Tyr Thr Thr Gly Tyr Ala Asp Ser Val
 50                  55                  60

Lys Gly Arg Phe Thr Val Ser Arg Asp Asn Ala Ile Cys Asn Ser Leu
65                  70                  75                  80

Tyr Leu Gln Met Asn Ser Leu Arg Pro Glu Asp Thr Ala Val Tyr Tyr
                85                  90                  95

Cys Ala Lys Ala Pro Ser Pro Arg Arg Val Ile Ile Glu Tyr Phe Asp
                100                 105                 110

Ser Asp Tyr Trp Gly Gly Thr Ser Leu Thr Val Ser Ser
            115                 120                 125

<210> SEQ ID NO 32
<211> LENGTH: 124
<212> TYPE: PRT
<213> ORGANISM: Artificial Sequence
<220> FEATURE:
<223> OTHER INFORMATION: Ab20 - Heavy chain

<400> SEQUENCE: 32

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp Tyr
                20                  25                  30

Ala Ile His Met Val Arg Gln Ala Pro Gly Lys Gly Leu Glu Trp Val
            35                  40                  45

Ser Gly Ile Ser Trp Asp Ser Tyr Thr Thr Gly Tyr Ala Asp Ser Val
50                  55                  60

Lys Gly Arg Phe Thr Val Ser Arg Asp Asn Ala Lys Asn Ser Leu Tyr
65                  70                  75                  80

Leu Gln Met Asn Ser Leu Arg Pro Glu Asp Thr Ala Val Tyr Tyr Cys
                85                  90                  95

Ala Lys Ala Pro Ser Pro Arg Arg Val His Glu Tyr Phe Asp Ser Asp
            100                 105                 110

Tyr Trp Gly Gln Gly Thr Ser Leu Thr Val Ser Ser
        115                 120

<210> SEQ ID NO 33
<211> LENGTH: 126
<212> TYPE: PRT
<213> ORGANISM: Artificial Sequence
<220> FEATURE:
<223> OTHER INFORMATION: Ab21 - Heavy chain

<400> SEQUENCE: 33

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp Tyr
                20                  25                  30

Ala Ile His Met Val Arg Gln Ala Pro Gly Lys Gly Leu Glu Trp Val
            35                  40                  45

Ser Gly Ile Ser Trp Asp Ser Tyr Thr Thr Gly Tyr Ala Asp Ser Val
50                  55                  60

Lys Gly Arg Phe Thr Val Ser Arg Asp Asn Ala Ile Cys Asn Ser Leu
65                  70                  75                  80

Tyr Leu Gln Met Asn Ser Leu Arg Pro Glu Asp Thr Ala Val Tyr Tyr
                85                  90                  95

Cys Ala Lys Ala Pro Ser Pro Arg Arg Val Ile Ile Glu Tyr Phe Asp
                100                 105                 110

Ser Asp Tyr Trp Gly Gln Gly Thr Ser Leu Thr Val Ser Ser
            115                 120                 125

<210> SEQ ID NO 34
<211> LENGTH: 125
<212> TYPE: PRT

```
<213> ORGANISM: Artificial Sequence
<220> FEATURE:
<223> OTHER INFORMATION: Ab22 - Heavy chain

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp Tyr
            20                  25                  30

Ala Ile His Met Val Arg Gln Ala Pro Gly Lys Gly Leu Glu Trp Val
        35                  40                  45

Ser Gly Ile Ser Trp Asp Ser Tyr Thr Thr Gly Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Pro Glu Asp Thr Ala Val Tyr Tyr Cys
                85                  90                  95

Ala Lys Ala Pro Ser Pro Arg Arg Val Ile Ile Glu Tyr Phe Asp Ser
            100                 105                 110

Asp Tyr Trp Gly Gln Gly Thr Ser Leu Thr Val Ser Ser
        115                 120                 125

<210> SEQ ID NO 35
<211> LENGTH: 127
<212> TYPE: PRT
<213> ORGANISM: Artificial Sequence
<220> FEATURE:
<223> OTHER INFORMATION: Ab23 - Heavy chain

<400> SEQUENCE: 35

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
            20                  25                  30

Ala Ile Ile Ile Met Val Arg Gln Ala Pro Gly Lys Gly Leu Glu Trp
        35                  40                  45

Val Ala Gly Ile Ser Trp Asp Ser Tyr Thr Thr Gly Tyr Ala Asp Ser
    50                  55                  60

Val Lys Gly Arg Phe Thr Val Ser Arg Asp Asn Ala Lys Asn Ser Leu
65                  70                  75                  80

Tyr Leu Gln Met Asn Ser Leu Arg Pro Glu Asp Thr Ala Val Tyr Tyr
                85                  90                  95

Cys Ala Ile Cys Ala Pro Ser Pro Arg Arg Val Ile Ile Glu Tyr Phe
            100                 105                 110

Gln Tyr Asp Tyr Trp Gly Gln Gly Thr Ser Leu Thr Val Ser Ser
        115                 120                 125

<210> SEQ ID NO 36
<211> LENGTH: 126
<212> TYPE: PRT
<213> ORGANISM: Artificial Sequence
<220> FEATURE:
<223> OTHER INFORMATION: Ab24 - Heavy chain

<400> SEQUENCE: 36

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
            20                  25                  30
```

```
Ala Ile His Met Val Arg Gln Ala Pro Gly Lys Gly Leu Glu Trp Val
        35                  40                  45
Ala Gly Ile Ser Trp Asp Ser Tyr Thr Thr Gly Tyr Ala Asp Ser Val
 50                  55                  60
Lys Gly Arg Phe Thr Val Ser Arg Asp Asn Ala Lys Asn Ser Leu Tyr
 65                  70                  75                  80
Leu Gln Met Asn Ser Leu Arg Pro Glu Asp Thr Ala Val Tyr Tyr Cys
                 85                  90                  95
Ala Ile Cys Ala Pro Ser Pro Arg Arg Val Ile Ile Glu Tyr Phe Gln
                100                 105                 110
Tyr Asp Tyr Trp Gly Gln Gly Thr Ser Leu Thr Val Ser Ser
            115                 120                 125
```

<210> SEQ ID NO 37
<211> LENGTH: 122
<212> TYPE: PRT
<213> ORGANISM: Artificial Sequence
<220> FEATURE:
<223> OTHER INFORMATION: Ab25 - Heavy chain

<400> SEQUENCE: 37

```
Asp Val Lys Leu Val Glu Ser Gly Gly Gly Leu Val Lys Pro Gly Gly
 1               5                  10                  15
Ser Leu Lys Leu Ser Cys Ala Ala Ser Gly Phe Thr Ser Ser Ser Tyr
                20                  25                  30
Ala Met Ser Trp Val Arg Gln Ser Pro Glu Ile Cys Arg Leu Glu Trp
            35                  40                  45
Val Ala Ser Ile Ser Ser Gly Gly Ser Thr Tyr Tyr Pro Asp Ser Val
 50                  55                  60
Lys Gly Arg Phe Thr Ile Ser Arg Asp Asn Ala Arg Asn Asn Leu Tyr
 65                  70                  75                  80
Leu Gln Met Ser Ser Leu Arg Ser Glu Asp Thr Ala Met Tyr Tyr Cys
                85                  90                  95
Val Arg Glu Asp Tyr His Gly Ser Ser Tyr Trp Tyr Phe Asp Val Trp
                100                 105                 110
Gly Ala Gly Thr Ile Val Thr Val Ser Ser
            115                 120
```

<210> SEQ ID NO 38
<211> LENGTH: 118
<212> TYPE: PRT
<213> ORGANISM: Artificial Sequence
<220> FEATURE:
<223> OTHER INFORMATION: Ab26 - Heavy chain

<400> SEQUENCE: 38

```
Gln Val Gln Leu Gln Gln Ser Gly Pro Glu Leu Met Lys Pro Gly Ala
 1               5                  10                  15
Ser Val Lys Ile Ser Cys Lys Ala Thr Gly Tyr Thr Phe Ser Ser His
                20                  25                  30
Trp Ile Glu Trp Val Lys Gln Arg Pro Gly His Gly Leu Glu Trp Ile
            35                  40                  45
Gly Glu Ile Leu Pro Gly Ser Gly Ser Thr Lys Tyr Asn Glu Lys Phe
 50                  55                  60
Lys Gly Lys Ala Thr Phe Thr Ala Asp Thr Ser Ser Asn Thr Val Tyr
 65                  70                  75                  80
Met Gln Leu Ser Ser Leu Thr Ser Glu Asp Ser Ala Val Tyr His Cys
```

```
                    85                  90                  95
Ala Arg Trp Ser Gln Val Ile Val Met Asp Tyr Trp Gly Gln Gly Thr
            100                 105                 110

Ser Leu Thr Val Ser Ser
            115

<210> SEQ ID NO 39
<211> LENGTH: 109
<212> TYPE: PRT
<213> ORGANISM: Artificial Sequence
<220> FEATURE:
<223> OTHER INFORMATION: Ab1 - Light chain

<400> SEQUENCE: 39

Gln Pro Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Leu Tyr Phe Cys Val Leu Trp Asp Ser Asn
                85                  90                  95

Arg Leu Val Phe Gly Gly Gly Thr Lys Leu Thr Val Leu
            100                 105

<210> SEQ ID NO 40
<211> LENGTH: 113
<212> TYPE: PRT
<213> ORGANISM: Artificial Sequence
<220> FEATURE:
<223> OTHER INFORMATION: Ab2 - Light chain
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 40

Glu Ile Gln Val Thr Gln Thr Ser Ser Leu Ser Ala Ser Leu Gly
1               5                   10                  15

Asp Arg Val Thr Ile Ser Cys Arg Ala Ser Gln Asp Ile Lys Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Ser Leu Thr Ile Asp Asn Leu Glu Gln
65                  70                  75                  80

Glu Asp Val Ala Thr Tyr Phe Cys Gln Gln Gly Thr Thr Leu Pro Thr
                85                  90                  95

Trp Thr Phe Gly Gly Gly Xaa Lys Val Glu Ile Xaa Arg Ala Asp Ala
            100                 105                 110

Ala
```

<210> SEQ ID NO 41
<211> LENGTH: 112
<212> TYPE: PRT
<213> ORGANISM: Artificial Sequence
<220> FEATURE:
<223> OTHER INFORMATION: Ab3 - Light chain
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 41

Glu Ile Gln Val Thr Gln Thr Thr Ser Ser Leu Ser Ala Ser Leu Gly
1               5                   10                  15

Asp Arg Xaa Thr Xaa Cys Arg Ala Ser Gln Asp Ile Lys Asn Tyr Xaa
            20                  25                  30

Asn Trp Tyr Gln Gln Lys Pro Asp Gly Thr Val Lys Leu Leu Ile Tyr
        35                  40                  45

Tyr Thr Ser Ser Leu His Ser Gly Val Pro Ser Arg Phe Ser Gly Ser
    50                  55                  60

Gly Ser Gly Thr Asp Tyr Ser Leu Thr Ile Ser Asn Leu Glu Gln Glu
65                  70                  75                  80

Asp Val Ala Thr Tyr Phe Cys Gln Gln Gly Thr Thr Leu Pro Thr Trp
                85                  90                  95

Thr Phe Gly Gly Gly Xaa Lys Val Glu Ile Lys Arg Ala Asp Gly Ala
            100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Ab4 - Light chain
<220> FEATURE:
<221> NAME/KEY: misc_feature
<222> LOCATION: (49)..(49)
<223> OTHER INFORMATION: Xaa can be any naturally occurring amino acid

<400> SEQUENCE: 42

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Xaa Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Arg Ser Asn
                85                  90                  95

Glu Asp Pro Phe Thr Phe Gly Ser Gly Thr Lys Leu Glu Ile Lys
             100                 105                 110

<210> SEQ ID NO 43
<211> LENGTH: 111
<212> TYPE: PRT
<213> ORGANISM: Artificial Sequence
<220> FEATURE:
<223> OTHER INFORMATION: Ab5 - Light chain
<220> FEATURE:
<221> NAME/KEY: misc_feature
<222> LOCATION: (49)..(49)
<223> OTHER INFORMATION: Xaa can be any naturally occurring amino acid

<400> SEQUENCE: 43

Asp Ile Val Leu Thr Gln Ser Pro Ala Ser Leu Ala Val Ser Leu Gly
1               5                   10                  15

Gln Arg Ala Thr Ile Ser Cys Lys Ala Ser His Ser Val Asp Tyr Asp
            20                  25                  30

Gly Asp Gly Tyr Met Asn Trp Tyr Gln Gln Lys Pro Gly Gln Pro Pro
        35                  40                  45

Xaa Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Gly Asp Pro Phe Pro Phe Gly Ser Gly Thr Lys Leu Glu Ile Lys
            100                 105                 110

<210> SEQ ID NO 44
<211> LENGTH: 111
<212> TYPE: PRT
<213> ORGANISM: Artificial Sequence
<220> FEATURE:
<223> OTHER INFORMATION: Ab6 - Light chain
<220> FEATURE:
<221> NAME/KEY: misc_feature
<222> LOCATION: (49)..(49)
<223> OTHER INFORMATION: Xaa can be any naturally occurring amino acid

<400> SEQUENCE: 44

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Gly Val Asp Phe Asp
            20                  25                  30

Gly Asp Ala Tyr Met Asn Trp Tyr Gln Gln Lys Pro Gly Gln Pro Pro
        35                  40                  45

Xaa Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Gly Asp Pro Phe Pro Phe Gly Ser Gly Thr Lys Leu Glu Ile Lys
            100                 105                 110

<210> SEQ ID NO 45
<211> LENGTH: 112
<212> TYPE: PRT
<213> ORGANISM: Artificial Sequence
<220> FEATURE:
<223> OTHER INFORMATION: Ab7 - Light chain

<400> SEQUENCE: 45

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp His Asp
            20                  25                  30

Gly Asn Gly Tyr Met Asn Trp Tyr Gln Gln Lys Pro Gly Gln Pro Pro
        35                  40                  45

Arg Leu Leu Ile Tyr Ala Ala Ser Asn Leu Glu Tyr Gly Ile Pro Val
    50                  55                  60

Arg Phe Ser Gly Ser Gly Ser Gly Thr Asp Phe Ile Leu Asn Ile Ile
65                  70                  75                  80

Ile Pro Val Glu Glu Glu Asp Ala Ala Thr Tyr Tyr Cys Gln Gln Ser
                85                  90                  95

Asp Gly Asp Pro Phe Pro Phe Gly Ser Gly Thr Lys Leu Glu Ile Lys
            100                 105                 110

<210> SEQ ID NO 46
<211> LENGTH: 112
<212> TYPE: PRT
<213> ORGANISM: Artificial Sequence
<220> FEATURE:
<223> OTHER INFORMATION: Ab8 - Light chain

<400> SEQUENCE: 46

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp His Asp
            20                  25                  30

Gly Asn Gly Tyr Met Asn Trp Tyr Gln Gln Lys Pro Gly Gln Pro Pro
        35                  40                  45

Arg Leu Leu Ile Tyr Ala Ala Ser Asn Leu Glu Ser Gly Ile Pro Val
    50                  55                  60

Arg Phe Arg Gly Ser Gly Ser Gly Thr Asp Phe Ile Leu Asn Ile His
65                  70                  75                  80

Pro Val Glu Glu Glu Asp Ala Ala Thr Tyr Tyr Cys Gln Gln Ser Asp
                85                  90                  95

Gly Asp Pro Phe Pro Phe Gly Ser Gly Thr Ile Cys Leu Glu Ile Lys
            100                 105                 110

<210> SEQ ID NO 47
<211> LENGTH: 113
<212> TYPE: PRT
<213> ORGANISM: Artificial Sequence
<220> FEATURE:
<223> OTHER INFORMATION: Ab9 - Light chain
<220> FEATURE:
<221> NAME/KEY: misc_feature
<222> LOCATION: (87)..(87)
<223> OTHER INFORMATION: Xaa can be any naturally occurring amino acid

<400> SEQUENCE: 47

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Asn Tyr Met Asn Trp Tyr Gln Gln Lys Pro Gly Gln Ser Pro
        35                  40                  45

Ile Cys Leu Leu Ile Tyr Ala Ala Ser Asn Leu Gln Ser Gly Ile Pro
            50                  55                  60

Ala Arg Phe Ser Gly Ser Gly Ser Gly Thr Asp Phe Thr Leu Asn Ile
65                  70                  75                  80

His Pro Val Glu Glu Xaa Ala Ala Thr Tyr Tyr Cys Gln Arg Ser
                85                  90                  95

Asn Glu Asp Pro Phe Thr Phe Gly Ser Gly Thr Ile Cys Leu Glu Ile
            100                 105                 110

Lys

<210> SEQ ID NO 48
<211> LENGTH: 109
<212> TYPE: PRT
<213> ORGANISM: Artificial Sequence
<220> FEATURE:
<223> OTHER INFORMATION: Ab-10 - Light chain

<400> SEQUENCE: 48

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asp Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Val Tyr Phe Cys Val Leu Trp Asp Ser Asn
                85                  90                  95

Arg Leu Val Phe Gly Gly Gly Thr Lys Leu Thr Val Leu
            100                 105

<210> SEQ ID NO 49
<211> LENGTH: 108
<212> TYPE: PRT
<213> ORGANISM: Artificial Sequence
<220> FEATURE:
<223> OTHER INFORMATION: Ab11 - Light chain

<400> SEQUENCE: 49

Ala Val Val Thr Gln Glu Ser Ile Leu Thr Thr Ser Pro Gly Glu Thr
1               5                   10                  15

Val Thr Leu Thr Cys Arg Ser Ser Thr Gly Ala Val Thr Thr Ser Asn
            20                  25                  30

Tyr Ala Asn Trp Val Gln Gln Lys Pro Asp His Leu Phe Thr Ser Leu
        35                  40                  45

Ile Gly Gly Ile Ser Asn Arg Val Pro Gly Val Pro Ala Arg Phe Ser
    50                  55                  60

Gly Ser Leu Ile Gly Asp Lys Val Ala Leu Thr Ile Ile Gly Thr Gln
65                  70                  75                  80

Thr Glu Asp Glu Ala Ile Tyr Phe Cys Ala Leu Trp Tyr Ser Asn His
                85                  90                  95

Leu Val Phe Gly Gly Gly Thr Lys Leu Thr Val Leu
            100                 105

<210> SEQ ID NO 50

```
<211> LENGTH: 108
<212> TYPE: PRT
<213> ORGANISM: Artificial Sequence
<220> FEATURE:
<223> OTHER INFORMATION: Ab12 - Light chain

<400> SEQUENCE: 50

Ala Val Val Thr Gln Glu Ser Ile Leu Thr Thr Ser Pro Gly Glu Thr
1               5                   10                  15

Val Thr Leu Thr Cys Arg Ser Ser Thr Gly Ala Val Thr Thr Ser Asn
            20                  25                  30

Tyr Ala Asn Trp Val Gln Glu Lys Pro Asp His Leu Phe Thr Gly Leu
        35                  40                  45

Ile Gly Gly Thr Asn Asn Arg Ala Pro Gly Val Pro Ala Arg Phe Ser
    50                  55                  60

Gly Ser Leu Ile Gly Asp Lys Ala Ala Leu Thr Ile Thr Gly Ala Gln
65                  70                  75                  80

Thr Glu Asp Glu Ala Ile Tyr Phe Cys Ala Leu Trp Tyr Ser Asn His
                85                  90                  95

Leu Val Phe Gly Gly Gly Thr Lys Leu Thr Val Leu
            100                 105

<210> SEQ ID NO 51
<211> LENGTH: 110
<212> TYPE: PRT
<213> ORGANISM: Artificial Sequence
<220> FEATURE:
<223> OTHER INFORMATION: Ab13 - Light chain

<400> SEQUENCE: 51

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Ile Cys Ala Ala Leu Thr Ile Thr Gly
65                  70                  75                  80

Ala Gln Thr Glu Asp Glu Ala Ile Tyr Phe Cys Ala Leu Trp Ser Asn
                85                  90                  95

Asn Lys Leu Val Phe Gly Gly Thr Lys Leu Thr Val Leu
            100                 105                 110

<210> SEQ ID NO 52
<211> LENGTH: 108
<212> TYPE: PRT
<213> ORGANISM: Artificial Sequence
<220> FEATURE:
<223> OTHER INFORMATION: Ab14 - Light chain

<400> SEQUENCE: 52

Ala Val Val Thr Gln Glu Ser Ala Leu Thr Thr Ser Pro Gly Glu Thr
1               5                   10                  15

Val Thr Leu Thr Cys Arg Ser Ser Thr Gly Ala Val Thr Thr Ser Asn
            20                  25                  30

Tyr Ala Asn Trp Val Gln Glu Lys Pro Asp His Leu Phe Thr Gly Leu
        35                  40                  45
```

```
Ile Gly Gly Thr Asn Asn Arg Ala Pro Gly Val Pro Ala Arg Phe Ser
        50                  55                  60

Gly Ser Leu Ile Gly Asp Lys Ala Ala Leu Thr Ile Thr Gly Ala Gln
65                  70                  75                  80

Thr Glu Asp Glu Ala Ile Tyr Phe Cys Ser Leu Trp Tyr Ser Asn His
                85                  90                  95

Leu Val Phe Gly Gly Gly Thr Lys Leu Thr Val Leu
                100                 105
```

<210> SEQ ID NO 53
<211> LENGTH: 107
<212> TYPE: PRT
<213> ORGANISM: Artificial Sequence
<220> FEATURE:
<223> OTHER INFORMATION: Ab15 - Light chain

<400> SEQUENCE: 53

```
Gln Ala Val Val Thr Gln Glu Ser Ala Leu Ser Pro Gly Glu Thr Val
1               5                   10                  15

Thr Leu Thr Cys Arg Ser Ser Thr Gly Ala Val Thr Thr Ser Asn Tyr
                20                  25                  30

Ala Thr Trp Val Gln Glu Lys Pro Asp His Leu Phe Thr Gly Leu Ile
            35                  40                  45

Gly Val Thr Asn Tyr Gly Pro Pro Gly Val Pro Ser Arg Phe Ser Gly
        50                  55                  60

Ser Leu Ile Gly Asp Lys Ala Ala Leu Thr Ile Thr Gly Ala Gln Thr
65                  70                  75                  80

Glu Glu Glu Ala Met Tyr Phe Cys Ala Leu Trp Asp Ser Asn His Pro
                85                  90                  95

Val Phe Gly Gly Gly Thr Lys Leu Thr Val Leu
                100                 105
```

<210> SEQ ID NO 54
<211> LENGTH: 110
<212> TYPE: PRT
<213> ORGANISM: Artificial Sequence
<220> FEATURE:
<223> OTHER INFORMATION: Ab16 - Light chain

<400> SEQUENCE: 54

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Thr Trp Val Gln Glu Lys Pro Asp His Leu Phe Thr Gly
            35                  40                  45

Leu Ile Gly Val Thr Asn Tyr Gly Pro Pro Gly Val Pro Ser Arg Phe
        50                  55                  60

Ser Gly Ser Leu Ile Gly Asp Lys Ala Ala Leu Thr Ile Thr Gly Ala
65                  70                  75                  80

Gln Thr Glu Glu Glu Ala Met Tyr Phe Cys Ala Leu Trp Asp Ser Asn
                85                  90                  95

Leu Ile Pro Val Phe Gly Gly Gly Thr Lys Leu Thr Val Leu
                100                 105                 110
```

<210> SEQ ID NO 55
<211> LENGTH: 112
<212> TYPE: PRT
<213> ORGANISM: Artificial Sequence

```
<220> FEATURE:
<223> OTHER INFORMATION: Ab17 - Light chain

<400> SEQUENCE: 55

Gln Ser Ala Leu Thr Gln Pro Ala Ser Val Ser Gly Ala Pro Gly Gln
1               5                   10                  15

Thr Val Ser Ile Ser Cys Thr Gly Trp Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Ser His Asn Thr Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Thr
                85                  90                  95

Leu Gly Val Val Val Glu Gly Gly Thr Ile Cys Leu Thr Val Leu
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: Ab18 - Light chain

<400> SEQUENCE: 56

Gln Ser Ala Leu Thr Gln Pro Ala Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Ala Val His Trp Tyr Gln Gln Leu Pro Gly Thr Ala Pro Lys Leu
            35                  40                  45

Leu Ile Tyr Asp Asp Asn Asn Arg Pro Ser Gly Val Pro Asp Arg Phe
        50                  55                  60

Ser Gly Ser Lys Ser Asp Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Ser
                85                  90                  95

Leu Ser Gly Ser Val Phe Gly Thr Gly Thr Lys Leu Thr Val Leu
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Ab19 - Light chain

<400> SEQUENCE: 57

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60
```

```
Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Arg Gly Val Val Phe Gly Gly Gly Thr Lys Leu Thr Val Leu
            100                 105                 110
```

<210> SEQ ID NO 58
<211> LENGTH: 111
<212> TYPE: PRT
<213> ORGANISM: Artificial Sequence
<220> FEATURE:
<223> OTHER INFORMATION: Ab20 - Light chain

<400> SEQUENCE: 58

```
Gln Ser Ala Leu Thr Gln Pro Ala Ser Val Ser Gly Ala Pro Gly Gln
 1               5                  10                  15

Arg Val Thr Met Ser Cys Thr Gly Ser Ser Ser Asn Ile Gly Ala Gly
                 20                  25                  30

Tyr Asp Val His Trp Tyr Gln Gln Leu Pro Gly Thr Ala Pro Lys Leu
             35                  40                  45

Leu Ile Phe Gly Asn Thr Asn Arg Pro Ser Gly Val Pro Asp Arg Phe
 50                  55                  60

Ser Ala Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Asn Ser
                 85                  90                  95

Leu Ser Gly Val Val Phe Gly Gly Gly Thr Lys Leu Thr Val Leu
            100                 105                 110
```

<210> SEQ ID NO 59
<211> LENGTH: 111
<212> TYPE: PRT
<213> ORGANISM: Artificial Sequence
<220> FEATURE:
<223> OTHER INFORMATION: Ab21 - Light chain

<400> SEQUENCE: 59

```
Gln Ser Ala Leu Thr Gln Pro Ala Ser Val Ser Gly Ala Pro Gly Gln
 1               5                  10                  15

Arg Val Thr Ile Ser Cys Thr Gly Ser Ser Ser Asn Ile Gly Ala Gly
                 20                  25                  30

Tyr Asp Val His Trp Tyr Gln Gln Leu Pro Gly Thr Ala Pro Lys Leu
             35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Val Val Phe Gly Gly Gly Thr Lys Leu Thr Val Leu
            100                 105                 110
```

<210> SEQ ID NO 60
<211> LENGTH: 110
<212> TYPE: PRT
<213> ORGANISM: Artificial Sequence
<220> FEATURE:
<223> OTHER INFORMATION: Ab22 - Light chain

```
<400> SEQUENCE: 60

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Trp Gly Asn Ser Asn Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Ser Gly Val Val Phe Gly Gly Gly Thr Lys Leu Thr Val Leu
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: Ab23 - Light chain

<400> SEQUENCE: 61

Gln Ser Ala Leu Thr Gln Pro Ala Ser Val Ser Gly Ala Pro Gly Gln
1               5                   10                  15

Thr Val Ser Ile Ser Cys Thr Gly Trp Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Ser Ile Ile Asn Thr Asn Arg Pro Ser Gly Val Pro Asp Arg
        50                  55                  60

Phe Ser Gly Ser Lys Ser Gly Thr Ser Ala Ser Leu Ala Ile Thr Gly
65                  70                  75                  80

Leu Gln Ala Glu Asp Glu Ala Asp Tyr Tyr Cys Gln Ser Tyr Asp Ser
                85                  90                  95

Thr Leu Gly Val Val Val Glu Gly Gly Gly Thr Lys Leu Thr Val Leu
            100                 105                 110

<210> SEQ ID NO 62
<211> LENGTH: 111
<212> TYPE: PRT
<213> ORGANISM: Artificial Sequence
<220> FEATURE:
<223> OTHER INFORMATION: Ab24 - Light chain

<400> SEQUENCE: 62

Gln Ser Ala Leu Thr Gln Pro Ala Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80
```

Gln Ala Glu Asp Glu Ala Asp Tyr Tyr Cys Gln Ser Tyr Asp Ser Ser
                85                  90                  95

Leu Ser Gly Val Val Phe Gly Gly Gly Thr Lys Leu Thr Val Leu
            100                 105                 110

<210> SEQ ID NO 63
<211> LENGTH: 113
<212> TYPE: PRT
<213> ORGANISM: Artificial Sequence
<220> FEATURE:
<223> OTHER INFORMATION: Ab25 - Light chain

<400> SEQUENCE: 63

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Ile Cys Leu Leu Ile Tyr Ala Ala Ser Asn Leu Glu Ser Gly Ile Pro
50                  55                  60

Ala Arg Phe Ser Gly Ser Gly Ser Gly Thr Asp Phe Thr Leu Asn Ile
65                  70                  75                  80

His Pro Val Glu Glu Glu Asp Ala Ala Thr Tyr Tyr Cys Gln Gln Ser
                85                  90                  95

Asn Glu Asp Pro Trp Thr Phe Gly Gly Gly Thr Lys Leu Glu Ile Lys
            100                 105                 110

Arg

<210> SEQ ID NO 64
<211> LENGTH: 103
<212> TYPE: PRT
<213> ORGANISM: Artificial Sequence
<220> FEATURE:
<223> OTHER INFORMATION: Ab26 - Light chain

<400> SEQUENCE: 64

Glu Ser Ala Leu Thr Thr Ser Pro Gly Glu Thr Val Thr Leu Thr Cys
1               5                   10                  15

Arg Ser Ser Thr Gly Ala Val Thr Thr Ser Asn Tyr Ala Asn Trp Val
                20                  25                  30

Gln Glu Lys Pro Asp His Leu Phe Thr Gly Leu Ile Gly Gly Thr Asn
            35                  40                  45

Asn Arg Ala Pro Gly Val Pro Ala Arg Phe Ser Gly Ser Leu Ile Gly
50                  55                  60

Asp Lys Ala Ala Leu Thr Ile Thr Gly Ala Gln Thr Glu Asp Glu Ala
65                  70                  75                  80

Asn Phe Cys Val Leu Trp Tyr Ser Asn Glu Ile Leu Val Phe Gly Gly
                85                  90                  95

Gly Thr Lys Leu Thr Val Leu
            100

<210> SEQ ID NO 65
<211> LENGTH: 8
<212> TYPE: PRT
<213> ORGANISM: Artificial Sequence
<220> FEATURE:
<223> OTHER INFORMATION: CDR1 HC UK6Mab01

<400> SEQUENCE: 65

```
Gly Tyr Thr Phe Ser Asn Tyr Trp
1               5
```

<210> SEQ ID NO 66
<211> LENGTH: 8
<212> TYPE: PRT
<213> ORGANISM: Artificial Sequence
<220> FEATURE:
<223> OTHER INFORMATION: CDR1 HC UK6Mab02

<400> SEQUENCE: 66

```
Gly Tyr Thr Phe Ser Ser Tyr Trp
1               5
```

<210> SEQ ID NO 67
<211> LENGTH: 8
<212> TYPE: PRT
<213> ORGANISM: Artificial Sequence
<220> FEATURE:
<223> OTHER INFORMATION: CDR1 HC Ab12

<400> SEQUENCE: 67

```
Gly Tyr Thr Phe Thr Ser Tyr Trp
1               5
```

<210> SEQ ID NO 68
<211> LENGTH: 8
<212> TYPE: PRT
<213> ORGANISM: Artificial Sequence
<220> FEATURE:
<223> OTHER INFORMATION: CDR2 CDR3 HC UK6Mab01

<400> SEQUENCE: 68

```
Ile Leu Pro Gly Thr Gly Arg Thr
1               5
```

<210> SEQ ID NO 69
<211> LENGTH: 8
<212> TYPE: PRT
<213> ORGANISM: Artificial Sequence
<220> FEATURE:
<223> OTHER INFORMATION: CDR2 CDR3 HC UK6Mab02

<400> SEQUENCE: 69

```
Ile Leu Pro Gly Ser Gly Asp Thr
1               5
```

<210> SEQ ID NO 70
<211> LENGTH: 8
<212> TYPE: PRT
<213> ORGANISM: Artificial Sequence
<220> FEATURE:
<223> OTHER INFORMATION: CDR2 CDR3 HC Ab12

<400> SEQUENCE: 70

```
Ile Asn Pro Ser Gly Gly Ser Thr
1               5
```

<210> SEQ ID NO 71
<211> LENGTH: 9
<212> TYPE: PRT
<213> ORGANISM: Artificial Sequence
<220> FEATURE:
<223> OTHER INFORMATION: CDR1 LC

<400> SEQUENCE: 71

```
Thr Gly Ala Val Thr Thr Ser Asn Tyr
1               5

<210> SEQ ID NO 72
<211> LENGTH: 9
<212> TYPE: PRT
<213> ORGANISM: Artificial Sequence
<220> FEATURE:
<223> OTHER INFORMATION: CDR1 LC

<400> SEQUENCE: 72

Thr Gly Ala Val Thr Ser Gly Asn Tyr
1               5

<210> SEQ ID NO 73
<211> LENGTH: 9
<212> TYPE: PRT
<213> ORGANISM: Artificial Sequence
<220> FEATURE:
<223> OTHER INFORMATION: CDR3 LC

<400> SEQUENCE: 73

Ala Leu Trp Tyr Ser Asn His Leu Val
1               5

<210> SEQ ID NO 74
<211> LENGTH: 9
<212> TYPE: PRT
<213> ORGANISM: Artificial Sequence
<220> FEATURE:
<223> OTHER INFORMATION: CDR3 LC

<400> SEQUENCE: 74

Ala Leu Trp Ser Asn Asn Lys Leu Val
1               5

<210> SEQ ID NO 75
<211> LENGTH: 9
<212> TYPE: PRT
<213> ORGANISM: Artificial Sequence
<220> FEATURE:
<223> OTHER INFORMATION: CDR3 LC

<400> SEQUENCE: 75

Ala Leu Trp Tyr Ser Asn Lys Leu Val
1               5
```

COMPOUNDS AND METHODS FOR USE IN CONNECTION WITH OPIOID USE DISORDERS

RELATED APPLICATIONS

This application claims priority from U.S. Provisional Application Ser. No. 63/032,995 filed Jun. 1, 2020, the entire disclosure of which is incorporated herein by this reference.

GOVERNMENT INTEREST

This invention was made with government support under grant number CHE-1111761 awarded by the National Science Foundation (NSF). The government has certain rights in the invention.

TECHNICAL FIELD

The presently-disclosed subject matter generally relates to opioid use disorders (OUDs). In particular, certain embodiments of the presently-disclosed subject matter relate compositions and methods for binding opioids while avoiding binding to OUD treatment agents.

INTRODUCTION

Opioid drugs, especially heroin,[1] are known as a growing national crisis in America due to the rapidly increasing overdose deaths.[2,3] The rapid increase in heroin overdose deaths is related to the fact that heroin is much cheaper and easy to obtain, compared to other opioid drugs. In fact, heroin has become much cheaper than any other drug of abuse, e.g. $10-$20 for a typical single dose (0.1 g) of heroin purchased on the street.[4] Notably, heroin itself is actually a prodrug and is converted by cholinesterases[5-6] to the highly active metabolites 6-monoacetylmorphine (6-MAM) and morphine, as depicted in FIG. 1.[7-10] Both 6-MAM and morphine have higher binding affinities with μ-opioid receptor compared to heroin itself.[11] So, both 6-MAM and morphine are responsible for the toxicity and physiological effects of heroin.[12-18] 6-MAM is mainly responsible for the acute toxicity of heroin due to its higher activity and shorter half-life, whereas morphine is mainly responsible for the long-term toxicity of heroin due to its longer half-life.[6] The opioid drugs exert their main physiological effects through activating μ-opioid receptor in the brain.

The well-known connection between heroin abuse and prescription opioid abuse is related to the actual availability and costs, in addition to the common brain protein targets (opioid receptors), of these opioid drugs. Indeed, "80% of recent heroin initiates reported that they began their opioid use through the nonmedical use of prescription opioid medications."[4] Those who abuse the prescription drugs most often obtain them from friends and family either through sharing or theft. When they are no longer able to get prescription opioid drugs, they start to use illegal opioid heroin, because heroin is easy to obtain and is relatively inexpensive.

Currently used therapeutic agents for treatment of opioid-induced disorders/toxicity include naloxone (a non-selective and competitive antagonist of opioid receptors) used for overdose treatment and buprenorphine (a partial agonist of μ-opioid receptor and an antagonist/partial agonist of many other receptors), methadone (an agonist of μ-opioid receptor, an antagonist of glutamatergic N-methyl-D-aspartate receptor, and a noncompetitive α3β4 neuronal nicotinic acetylcholine receptor), and naltrexone (a competitive antagonist of μ-opioid receptor and other opioid receptors) used for opioid dependence treatment.

These therapeutic agents may be used in various formulations/devices, such as a nasal spray device for naloxone[19] for fast toxicity treatment and extended-release naltrexone for relapse-preventing opioid dependence treatment.[20] All of these therapeutic agents in current clinical use, and most of other therapeutic candidates under preclinical/clinical development, bind to opioid receptors (and/or related receptors) in the brain and, thus, block/regulate the physiological effects of opioid in the body.

The overdose treatment with naloxone appears to be effective in many cases, however, the naloxone must be introduced relatively quickly following an opioid overdose to revive subject who is overdosing. Further, once overdosed, heroin-dependent users may continue to overdose again and again until a fatal overdose. Some heroin-dependent users survived from one overdose with treatment in a hospital, and then died of another overdose the next day.[4] Even worse, the use of naltrexone or its extended-release formulation Vivitrol actually increased heroin overdose.[21-23]

A truly effective heroin treatment should account for not only rescuing heroin users who have already been overdosed, but also preventing the users from overdose again. In particular, it would be desirable to identify alternative therapeutic strategies to complement the traditional μ-opioid receptor antagonist approach for treatment of heroin-related opioid overdose and dependence.

As alternatives to the traditional μ-opioid receptor antagonist approach, vaccines (that help to elicit antibodies against specific antigens in the body) and monoclonal antibodies (mAbs, for use as the passive vaccination/immunity) have been being developed for treatment of opioid use disorders (OUDs).[24-34] A vaccine could be effective for dependency treatment, but would require an immune response to be effective and, thus, would not be useful for overdose treatment. An mAb could be useful for treatment of both the drug dependence and overdose. In particular, an exogenous mAb, which may be used as an exogenous protein therapeutic, is not expected to cross blood-brain barrier (BBB) to interact with any receptors in the brain. Instead, through tightly binding with the opioid drugs in the plasma, the exogenous antibodies are expected to decrease the concentrations of freely available opioids and, thus, attenuate the toxicity and physiological effects of the opioid drugs.

Concerning the feasibility for using an mAb to attenuate the drug toxicity for overdose treatment in addition to the dependence treatment, Janda and associates have demonstrated in mice that an anti-cocaine mAb can be used as an effective antidote to rescue mice after the mice were given a lethal dose of cocaine (post-exposure treatment)[35] Based on their encouraging animal data, Janda et al. concluded that "minimal antibody doses were shown to counteract the lethality of a molar excess of circulating cocaine" in the case of the post-exposure treatment and "Passive vaccination with drug-specific antibodies represents a viable treatment strategy for the human condition of cocaine overdose."[35] The work reported by Janda et al. have demonstrated the general concept of utilizing an mAb as a feasible antidote to counteract the drug toxicity post-exposure. Thus, as disclosed herein, it is reasonable to apply a similar concept to an anti-opioid mAb as an antidote to counteract opioid toxicity for overdose treatment, in addition to the dependency treatment.

In fact, there have been various reports of efforts to generate mAbs specifically against morphine[25-30,36] or 6-MAM.[31-33] Of the anti-morphine mAbs reported so far, a single chain Fv antibody[30] can also bind with heroin. However, there has been no demonstration that any of the reported anti-morphine mAbs[25-30, 34] can bind with 6-MAM. Conversely, the reported anti-6-MAM mAbs[31-33] specifically recognize 6-MAM, but not morphine.

There has been no demonstration that any of the mAbs reported so far[25-33, 36] can bind with both 6-MAM (which is mainly responsible for the acute toxicity of heroin) and morphine (which is mainly responsible for the long-term toxicity of heroin), let alone binding with all of the three heroin-related opioids (6-MAM, morphine, and heroin itself).

Interestingly, the 6-MAM-specific mAb (known as 6-MAM-214, with an affinity of 0.3 μM or 300 nM for 6-MAM) was indeed able to reduce the acute heroin effects in mice.[31] Thus, as contemplated and described herein, it is possible that a mAb capable of binding with all the three heroin-related opioids (6-MAM, morphine, and heroin itself) would be able to more effectively attenuate the toxicity (including both the acute and long-term toxicity) and physiological effects of heroin.

In general, it is increasingly interesting to develop mAbs as therapeutic proteins. Usually, antibodies may be generated either in vitro, such as the phage and yeast surface display, or in vivo through animal immunization and antibody screening using enzyme-linked immunosorbent assay (ELISA) or Western blot assays, followed by humanization of the identified animal antibody.[37]

There are a lot of challenges in generating mAbs for therapeutic applications. For example, using the in vivo approach during the antibody discovery stage, immunization affords limited control over antibody affinity and specificity due to the difficulty in controlling antigen presentation to the immune system. Using in vitro methods such as the phage and yeast surface display, a display method is limited by the need of screening a large library etc.[37] Hence, it is understandable that none of the mAbs reported so far has demonstrated the ability to bind with all of the three heroin-related opioids (6-MAM, morphine, and heroin itself) or even the ability to bind with both 6-MAM and morphine. Accordingly, there is an unmet need in the art.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes monoclonal antibodies (mAb) having the ability to bind with one, two, or all three of the heroin-related opioids (6-MAM, morphine, and heroin itself). For example, in some embodiments, the mAb bind with both 6-MAM and morphine. In some embodiments, the mAb binds one or more of the heroin-related opioids, and also does not affect opioid use disorder (OUD) treatment options, such as naloxone and naltrexone. The studies described herein were developed to identify/design an mAb capable of potently binding with all the heroin-related opioids without binding with naloxone and naltrexone.

Also disclosed herein is a general, systematic structure-based virtual screening and design approach for identification of useful antibodies. Exemplary antibodies identified by this process and disclosed herein include UK6Mab01 (a partially humanized antibody) and UK6Mab02 (a fully humanized antibody), which are capable of binding to multiple addictive opioids (including 6-MAM, morphine, heroin, hydrocodone, oxycodone, meperidine, and fentanyl) without significant binding with OUD treatment agents naloxone and naltrexone. Accordingly, antibodies of the presently-disclosed subject matter and as identified by the presently-disclosed methods can serve in connection with treatment of OUDs.

As disclosed herein, the experimental binding affinities reasonably correlate with the computationally predicted binding free energies. Further, the experimental activity data strongly support the computational predictions, establishing that the systematic structure-based virtual screening and humanization design protocol is reliable. The general, systematic structure-based virtual screening and design approach as disclosed herein will be useful for many other antibody selection and design efforts.

The presently-disclosed subject matter includes methods of identifying antibodies that bind an opioid without significant binding with treatment agents for opioid use disorder (OUD). The presently-disclosed subject matter further includes antibodies, and compositions including such antibodies, for use in treating OUD. The presently-disclosed subject matter further includes methods for treating OUD. The presently-disclosed subject matter further includes methods for detecting an opioid in a sample.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 3A-3D. The predicted binding modes of Ab13 with 6-MAM (FIGS. 3A and 3B for two slightly different orientations) and heroin (FIG. 3D), as well as the X-ray crystal structure of morphine with Ab13 (FIG. 3C) (PDB ID: 1Q0Y). Dashed lines indicate the hydrogen bonds.

FIG. 5A-5K. (FIG. 5A) SDS-PAGE analysis of the purified UK6Mab01 and UK6Mab02 under the reducing condition. (FIG. 5B) Saturation binding of UK6Mab01 with 2 nM [$H^3$]-morphine. (FIG. 5C) Saturation binding of UK6Mab02 with 2 nM [$H^3$]-morphine. (FIGS. 5D-5F) Competitive binding of 2 nM [$H^3$]-morphine against 6-MAM (FIG. 5D), heroin (FIG. 5E) and hydrocodone (FIG. 5F) with UK6Mab01 (20 nM). (FIGS. 5G-5I) Competitive binding of 2 nM [$H^3$]-morphine against 6-MAM (FIG. 5G), heroin (FIG. 5H), and hydrocodone (FIG. 5I) with UK6Mab02 (60 nM). (FIG. 5J) Screening of UK6Mab01 and UK6Mab02 against other drugs. (FIG. 5K) The correlation of the predicted binding free energies with the experimentally derived binding free energies (converted from the experimental binding affinities using the well-known thermodynamic equation) with 6-MAM. The concentrations of the antibody, [$H^3$]-morphine, and the competing drug were 60 nM, 2 nM, and 10 μM, respectively. 10 μM morphine and deionized water were set as positive and negative controls and normalized to the 100% and 0% inhibition rates, respectively. All experiments were performed in triplicate. The experimental data were analyzed with the GraphPad Prism 7 software to determine the $K_d$ values.

BRIEF DESCRIPTION OF THE SEQUENCE LISTING

Figure 4A:
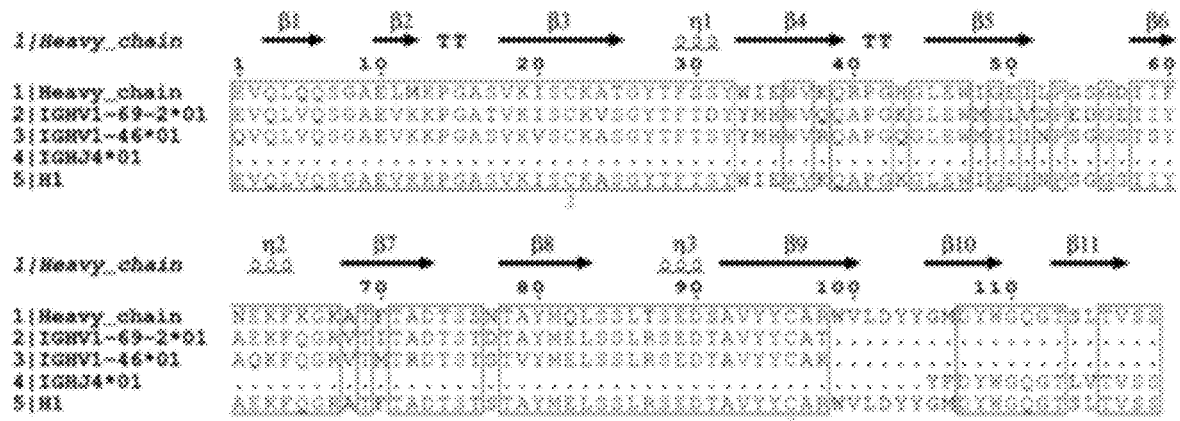
FIGS. 4A and 4B. Alignment of amino-acid sequences of Ab13, top-ranked human antibodies, and the humanized antibodies. The heavy chain sequences (SEQ ID NOs: 1-5) presented in FIG. 4A and the light chain sequences (SEQ ID NOs: 6-12) are presented in FIG. 4B. Highly similar residues are framed in boxes. The arrow, "TT" and helix indicate the β-sheets, turns and α-helixes domain of Ab13. "1" indicates disulfide linkage within the heavy chain or light chain.
Figure 4B:
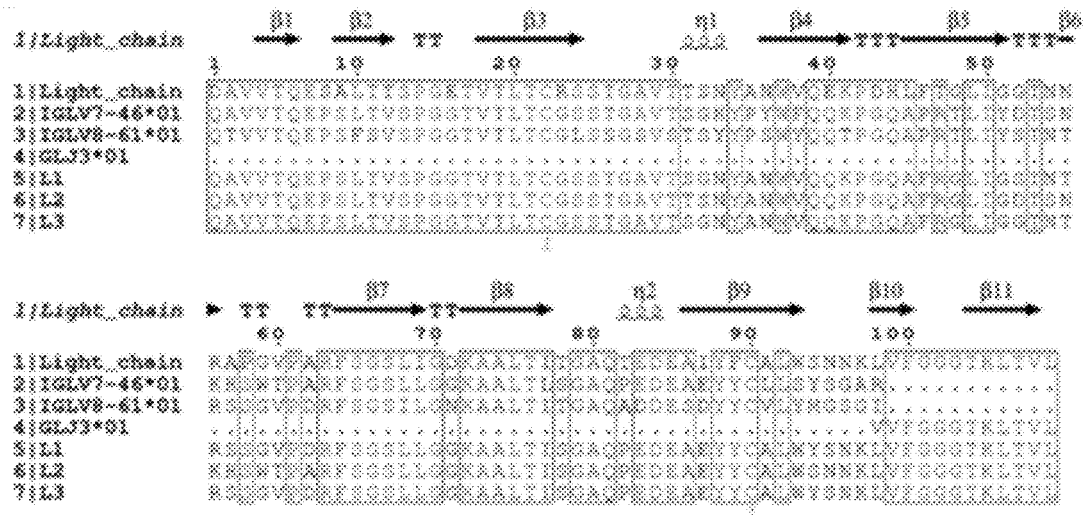

SEQ ID NO: 1 is the sequence included in a heavy chain sequence of an antibody, which is set forth in FIG. 4A.
SEQ ID NO: 2 is the sequence included in a heavy chain sequence of an antibody, which is set forth in FIG. 4A.
SEQ ID NO: 3 is the sequence included in a heavy chain sequence of an antibody, which is set forth in FIG. 4A.
SEQ ID NO: 4 is the sequence included in a heavy chain sequence of an antibody, which is set forth in FIG. 4A.
SEQ ID NO: 5 is the sequence included in a heavy chain sequence of an antibody, which is set forth in FIG. 4A.
SEQ ID NO: 6 is the sequence included in a light chain sequence of an antibody, which is set forth in FIG. 4B.
SEQ ID NO: 7 is the sequence included in a light chain sequence of an antibody, which is set forth in FIG. 4B.
SEQ ID NO: 8 is the sequence included in a light chain sequence of an antibody, which is set forth in FIG. 4B.
SEQ ID NO: 9 is the sequence included in a light chain sequence of an antibody, which is set forth in FIG. 4B.
SEQ ID NO: 10 is the sequence included in a light chain sequence of an antibody, which is set forth in FIG. 4B.
SEQ ID NO: 11 is the sequence included in a light chain sequence of an antibody, which is set forth in FIG. 4B.
SEQ ID NO: 12 is the sequence included in a light chain sequence of an antibody, which is set forth in FIG. 4B.
SEQ ID NO: 13 is the sequence included in a heavy chain sequence of an antibody, which is set forth in Table 1.
SEQ ID NO: 14 is the sequence included in a heavy chain sequence of an antibody, which is set forth in Table 1.
SEQ ID NO: 15 is the sequence included in a heavy chain sequence of an antibody, which is set forth in Table 1.
SEQ ID NO: 16 is the sequence included in a heavy chain sequence of an antibody, which is set forth in Table 1.
SEQ ID NO: 17 is the sequence included in a heavy chain sequence of an antibody, which is set forth in Table 1.
SEQ ID NO: 18 is the sequence included in a heavy chain sequence of an antibody, which is set forth in Table 1.
SEQ ID NO: 19 is the sequence included in a heavy chain sequence of an antibody, which is set forth in Table 1.
SEQ ID NO: 20 is the sequence included in a heavy chain sequence of an antibody, which is set forth in Table 1.
SEQ ID NO: 21 is the sequence included in a heavy chain sequence of an antibody, which is set forth in Table 1.
SEQ ID NO: 22 is the sequence included in a heavy chain sequence of an antibody, which is set forth in Table 1.
SEQ ID NO: 23 is the sequence included in a heavy chain sequence of an antibody, which is set forth in Table 1.
SEQ ID NO: 24 is the sequence included in a heavy chain sequence of an antibody, which is set forth in Table 1.
SEQ ID NO: 25 is the sequence included in a heavy chain sequence of an antibody, which is set forth in Table 1.
SEQ ID NO: 26 is the sequence included in a heavy chain sequence of an antibody, which is set forth in Table 1.
SEQ ID NO: 27 is the sequence included in a heavy chain sequence of an antibody, which is set forth in Table 1.
SEQ ID NO: 28 is the sequence included in a heavy chain sequence of an antibody, which is set forth in Table 1.
SEQ ID NO: 29 is the sequence included in a heavy chain sequence of an antibody, which is set forth in Table 1.
SEQ ID NO: 30 is the sequence included in a heavy chain sequence of an antibody, which is set forth in Table 1.
SEQ ID NO: 31 is the sequence included in a heavy chain sequence of an antibody, which is set forth in Table 1.
SEQ ID NO: 32 is the sequence included in a heavy chain sequence of an antibody, which is set forth in Table 1.
SEQ ID NO: 33 is the sequence included in a heavy chain sequence of an antibody, which is set forth in Table 1.
SEQ ID NO: 34 is the sequence included in a heavy chain sequence of an antibody, which is set forth in Table 1.
SEQ ID NO: 35 is the sequence included in a heavy chain sequence of an antibody, which is set forth in Table 1.
SEQ ID NO: 36 is the sequence included in a heavy chain sequence of an antibody, which is set forth in Table 1.
SEQ ID NO: 37 is the sequence included in a heavy chain sequence of an antibody, which is set forth in Table 1.
SEQ ID NO: 38 is the sequence included in a heavy chain sequence of an antibody, which is set forth in Table 1.
SEQ ID NO: 39 is the sequence included in a light chain sequence of an antibody, which is set forth in Table 1.
SEQ ID NO: 40 is the sequence included in a light chain sequence of an antibody, which is set forth in Table 1.
SEQ ID NO: 41 is the sequence included in a light chain sequence of an antibody, which is set forth in Table 1.
SEQ ID NO: 42 is the sequence included in a light chain sequence of an antibody, which is set forth in Table 1.
SEQ ID NO: 43 is the sequence included in a light chain sequence of an antibody, which is set forth in Table 1.
SEQ ID NO: 44 is the sequence included in a light chain sequence of an antibody, which is set forth in Table 1.
SEQ ID NO: 45 is the sequence included in a light chain sequence of an antibody, which is set forth in Table 1.
SEQ ID NO: 46 is the sequence included in a light chain sequence of an antibody, which is set forth in Table 1.
SEQ ID NO: 47 is the sequence included in a light chain sequence of an antibody, which is set forth in Table 1.

SEQ ID NO: 48 is the sequence included in a light chain sequence of an antibody, which is set forth in Table 1.

SEQ ID NO: 49 is the sequence included in a light chain sequence of an antibody, which is set forth in Table 1.

SEQ ID NO: 50 is the sequence included in a light chain sequence of an antibody, which is set forth in Table 1.

SEQ ID NO: 51 is the sequence included in a light chain sequence of an antibody, which is set forth in Table 1.

SEQ ID NO: 52 is the sequence included in a light chain sequence of an antibody, which is set forth in Table 1.

SEQ ID NO: 53 is the sequence included in a light chain sequence of an antibody, which is set forth in Table 1.

SEQ ID NO: 54 is the sequence included in a light chain sequence of an antibody, which is set forth in Table 1.

SEQ ID NO: 55 is the sequence included in a light chain sequence of an antibody, which is set forth in Table 1.

SEQ ID NO: 56 is the sequence included in a light chain sequence of an antibody, which is set forth in Table 1.

SEQ ID NO: 57 is the sequence included in a light chain sequence of an antibody, which is set forth in Table 1.

SEQ ID NO: 58 is the sequence included in a light chain sequence of an antibody, which is set forth in Table 1.

SEQ ID NO: 59 is the sequence included in a light chain sequence of an antibody, which is set forth in Table 1.

SEQ ID NO: 60 is the sequence included in a light chain sequence of an antibody, which is set forth in Table 1.

SEQ ID NO: 61 is the sequence included in a light chain sequence of an antibody, which is set forth in Table 1.

SEQ ID NO: 62 is the sequence included in a light chain sequence of an antibody, which is set forth in Table 1.

SEQ ID NO: 63 is the sequence included in a light chain sequence of an antibody, which is set forth in Table 1.

SEQ ID NO: 64 is the sequence included in a light chain sequence of an antibody, which is set forth in Table 1.

SEQ ID NO: 65 is the sequence of a complementarity-determining regions (CDRs) of the heavy chain of an antibody as disclosed herein.

SEQ ID NO: 66 is the sequence of a complementarity-determining regions (CDRs) of the heavy chain of an antibody as disclosed herein.

SEQ ID NO: 67 is the sequence of a complementarity-determining regions (CDRs) of the heavy chain of an antibody as disclosed herein.

SEQ ID NO: 68 is the sequence of a complementarity-determining regions (CDRs) of the heavy chain of an antibody as disclosed herein.

SEQ ID NO: 69 is the sequence of a complementarity-determining regions (CDRs) of the heavy chain of an antibody as disclosed herein.

SEQ ID NO: 70 is the sequence of a complementarity-determining regions (CDRs) of the heavy chain of an antibody as disclosed herein.

SEQ ID NO: 71 is the sequence of a complementarity-determining regions (CDRs) of the light chain of an antibody as disclosed herein.

SEQ ID NO: 72 is the sequence of a complementarity-determining regions (CDRs) of the light chain of an antibody as disclosed herein.

SEQ ID NO: 73 is the sequence of a complementarity-determining regions (CDRs) of the light chain of an antibody as disclosed herein.

SEQ ID NO: 74 is the sequence of a complementarity-determining regions (CDRs) of the light chain of an antibody as disclosed herein.

SEQ ID NO: 75 is the sequence of a complementarity-determining regions (CDRs) of the light chain of an antibody as disclosed herein.

This application contains a sequence listing submitted in accordance with 37 C.F.R. 1.821, named Zhan UKRF 2462 Sequence Listing_ST25.txt, created on Jun. 1, 2021, having a size of 72 KB, which is incorporated herein by this reference.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods of identifying antibodies that bind an opioid without significant binding with treatment agents for opioid use disorder (OUD).

In some embodiments, the method involves: (a) identifying computationally-refined structures of candidate mAbs using amino-acid sequences of variable domains of the mAbs, homology models of the antibodies, and energy-minimization; (b) superimposing X-ray crystal structures of an opioid with the computationally-refined structures of the candidate mAbs to simulate binding of opioid and antibodies to create opioid-antibody complex structures having one or more binding poses; (c) conducting energy minimization for each binding pose of each opioid-antibody complex structure; (d) calculating binding free energy of each binding pose of each opioid-antibody complex structure; and (e) select the antibodies associated with the binding pose having low binding free energy. In some embodiments, the opioid is one or more of 6-MAM, morphine, heroin, hydrocodone, oxycodone, meperidine, and fentanyl.

In some embodiments, the method also involves determining actual binding affinity of each predicted antibody by preparing and testing each predicted antibody. In some embodiments, the opioid is one or more of 6-MAM, morphine, heroin, hydrocodone, oxycodone, meperidine, and fentanyl.

In some embodiments, the method also involves determining the binding affinity of each predicted antibody with a treatment agent for OUD. In some embodiments, the treatment agent for OUD is naloxone and/or and naltrexone. The presently-disclosed subject matter further includes antibodies, and compositions including such antibodies, for use in treating OUD. In some embodiments, the antibody is discovered by a method as disclosed herein. In some embodiments, the antibody is UK6Mab01 or UK6Mab02.

The presently-disclosed subject matter includes an isolated antibody or antigen fragment thereof that binds one or more of 6-MAM, morphine, heroin, hydrocodone, oxycodone, meperidine, and fentanyl, and does not bind naloxone or naltrexone. In some embodiments, the antibody is selected from the group consisting of: (a) an antibody comprising the sequence of SEQ ID NO: 5; (b) an antibody comprising the sequence of SEQ ID NO: 12; (c) an antibody comprising the sequence of SEQ ID NOs: 5 and 12; (d) an antibody comprising the sequence of SEQ ID NO: 25; (e) an antibody comprising the sequence of SEQ ID NO: 51; (f) an antibody comprising the sequence of SEQ ID NO: 25 and 51; (g) an antibody comprising the sequence of (i) SEQ ID NO: 65, 66, or 67, and (ii) SEQ ID NO: 68, 69, or 70; (h) an antibody comprising the sequence of (i) SEQ ID NO: 71 or 72, (ii) GTN, STN, or DTS, and (iii) SEQ ID NO: 73, 74, or 75; and (i) an antibody comprising the sequence of (i) SEQ ID NO: 65, 66, or 67, (ii) SEQ ID NO: 68, 69, or 70, (iii) SEQ ID NO: 71 or 72, (iv) GTN, STN, or DTS, and (v) SEQ ID NO: 73, 74, or 75. In some embodiments, the antibody comprises a sequence selected from the group consisting of the sequence of any one of SEQ ID NOS: 1-75.

The presently-disclosed subject matter further includes methods for treating OUD, which involve administering an antibody as disclosed herein to a subject in need thereof.

The presently-disclosed subject matter further includes methods for detecting an opioid in a sample, which includes contacting the sample with an antibody as disclosed herein, and detecting binding of the antibody to a ligand.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this application.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

An "antibody" is an immunoglobulin molecule capable of specific binding to a target, such as a carbohydrate, polynucleotide, lipid, polypeptide, etc., through at least one antigen recognition site, located in the variable domain of the immunoglobulin molecule. As used herein, the term encompasses not only intact polyclonal or monoclonal antibodies, but also, unless otherwise specified, any antigen-binding portion thereof that competes with the intact antibody for specific binding, fusion proteins comprising an antigen-binding portion, and any other modified configuration of the immunoglobulin molecule that comprises an antigen recognition site. Antigen-binding portions include, for example, Fab, Fab', F(ab')2, Fd, Fv, domain antibodies (dAbs, e.g., shark and camelid antibodies), portions including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. Depending on the antibody amino acid sequence of the constant region of its heavy chains, immunoglobulins can be assigned to different classes. There are five major classes (i.e., isotypes) of immunoglobulins: IgA, IgD, IgE, IgG, and IgM, and several of these may be further divided into subclasses (subtypes), e.g., $IgG_1$, $IgG_2$, $IgG_3$, $IgG_4$, $IgA_1$ and $IgA_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

The terms "antigen-binding portion" or "antigen-binding fragment" of an antibody (or simply "antibody portion"), as used interchangeably herein, refers to one or more portions of an antibody that retain the ability to specifically bind to an antigen (e.g., delta-CN). It has been shown that the antigen-binding function of an antibody can be performed by portions of a full-length antibody.

A "variable domain" of an antibody refers to the variable domain of the antibody light chain ($V_L$) or the variable domain of the antibody heavy chain ($V_H$), either alone or in combination. As known in the art, the variable domains of the heavy and light chains each consist of four framework regions (FRs) connected by three complementarity determining regions (CDRs) also known as hypervariable regions, and contribute to the formation of the antigen-binding site of antibodies. If variants of a subject variable domain are desired, particularly with substitution in amino acid residues outside a CDR (i.e., in the framework region), appropriate amino acid substitution, in some embodiments, conservative amino acid substitution, can be identified by comparing the subject variable domain to the variable domains of other antibodies which contain CDR1 and CDR2 sequences in the same canonical class as the subject variable domain.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "antigen (Ag)" refers to the molecular entity used for immunization of an immunocompetent vertebrate to produce the antibody (Ab) that recognizes the Ag or to screen an expression library (e.g., phage, yeast or ribosome display library, among others). Herein, Ag is termed more broadly and is generally intended to include target molecules that are specifically recognized by the Ab, thus including portions or mimics of the molecule used in an immunization process for raising the Ab or in library screening for selecting the Ab.

Generally, the term "epitope" refers to the area or region of an antigen to which an antibody specifically binds, i.e., an area or region in physical contact with the antibody. Thus, the term "epitope" refers to that portion of a molecule capable of being recognized by and bound by an antibody at one or more of the antibody's antigen-binding regions.

An antibody that "preferentially binds" or "specifically binds" or "selectively bind" (used interchangeably herein) to an epitope is a term well understood in the art, and methods to determine such specific or preferential binding are also well known in the art. A molecule is said to exhibit "specific binding," "selective binding," or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. Also, an antibody "specifically binds" or "preferentially binds" to a target if it binds with greater affinity, avidity, more readily, and/or with greater duration to that target in a sample than it binds to other substances present in the sample. As such, "specific binding" or "preferential binding" does not necessarily require (although it can include) exclusive binding.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. In some embodiments, diluents for aerosol or parenteral administration are phosphate buffered saline (PBS) or normal (0.9%) saline. Compositions comprising such carriers are formulated by well-known conventional methods.

The presently-disclosed subject matter is further illustrated by the following specific but non-limiting examples. The following examples may include compilations of data that are representative of data gathered at various times during the course of development and experimentation related to the present invention.

EXAMPLES

Example 1: General Strategy of the Systematic Structure-Based Virtual Screening for mAb Selection Antibodies, including a total of five classes, i.e. immunoglobulin (Ig)A, IgD, IgE, IgG, and IgM, are known as affinity proteins that are a key component of the adaptive immune system.[37] The ability of antibodies to bind to foreign invaders with high affinity and specificity is central to their functions. IgGs, including four subclasses, i.e. IgG1 to 4, are the most abundant class of antibodies, constituting approximately 75% of the serum immunoglobulin repertoire. Notably, all IgGs share the same overall architecture, with differences only in six loops known as the complementarity-determining regions (CDRs) in the antigen-binding site.

Utilizing these remarkable structural features, the general strategy of the systematic structure-based virtual screening approach to antibody selection and identification as disclosed herein starts from collection and structural modeling of all mAbs whose amino-acid sequences (particularly the six CDRs) are available, with a view toward identifying the available mAbs can meet the above-mentioned goal—capable of potently binding with all the heroin-related opioids without binding with naloxone and naltrexone. Using the modeled structure of each mAb available, one can dock each of the interested ligands (i.e. 6-MAM, heroin, morphine, naloxone, and naltrexone in the current study) to the antigen-binding site and carry out further simulations and calculations to computationally estimate the binding free energy with each ligand. Based on the computationally estimated binding free energies, one can predict which mAb most likely can meet the goal of the potency and selectivity.

Specific for the need of binding with multiple opioids, the computationally estimated binding free energies clearly indicated which mAb should have the highest overall potency for binding with 6-MAM, morphine, and heroin without significant binding affinity to naloxone and naltrexone. The computationally selected most promising mAb was modeled further for humanization, and the predicted humanized mAb was prepared and tested in vitro for its actual binding affinities with various ligands including 6-MAM, heroin, morphine, naloxone, and naltrexone etc. Described below are the detailed procedures of the used computational methods.

Example 2: Modeling of the Antibody Structures

The amino-acid sequences of variable domains of the antibodies were obtained from the IMGT/LIGM-DB database (imgt.org)[38] or manually collected from the references cited (see Tables 1 and 2). The homology models of antibodies were built using the PIGSpro software[39] which includes known X-ray crystal structures of a number of antibodies. Using the software, for homology modeling of each antibody structure, the template (used for the framework structure modeling) was selected based on the sequence alignment with those of the known X-ray crystal structure, the loops were kept in the similar canonical structure of template for the loop modeling method, and all other parameters were set as the default of the software.

Then the initial homology models were refined by performing a series of energy minimization processes. Specifically, the Amber14SB force field[40] was applied for the proteins in vacuo using AmberTools18.[41] The nonbonded cutoff for the real-space interactions was set to 10 Å. Two stages of energy minimization were conducted using a hybrid protocol of 8000 steps of steepest descent minimization followed by a conjugate gradient minimization until the convergence criterion (the root-mean-square of the energy gradient is less than $1.0 \times 10^{-4}$ kcal/mol·Å) was satisfied or the maximum of 2000 iteration steps was reached. During the energy minimization, a force constant of 10 kcal/mol·Å$^2$ was applied on the antibody backbone atoms. Then the final conformations were used for virtual screening described below.

Example 3: Virtual Selection of an Antibody Capable of Selectively Binding with Heroin-Related Opioids The computationally refined antibody structures were superimposed with the X-ray crystal structure of the complex of morphine with antibody 9B1[34] (PDB: 1Q0Y) using the PyMol software[42] in order to transform the atomic coordinates of all proteins into the same coordinate system with a commonly defined center of box required to define for systematic molecular docking, and the MglTools[43] software was used to prepare the protein and ligand pdbqt files for the docking. During the docking, the binding site was determined based on the antibody-morphine complex in 9B1 (PDB: 1Q0Y), the geometric center of the co-crystallized antibody-morphine complex was indicated as the active center of the docking box (the size_x, size_y, and size_z were set to 30, 30, and 30, respectively) which was large enough to cover the entire region of the binding site.

The docking calculations were conducted by using the AutoDock Vina software,[43] and all the default parameters were adopted. For each antibody-ligand complex, the top-4 ranked binding poses of the complex were selected for further computational evaluation in multiple steps.

First, the selected complex structures were energy-minimized using the same approach as described above for the energy-minimization of antibody structures without a ligand. The general Amber force field (gaff)[44] was used for the ligands. Second, the energy-minimized complex structure was relaxed by performing a short (20 ps) molecular dynamics (MD) simulation using the SANDER module of the AmberTools18 software[41] in vacuo with a constant temperature (T=300 K). A restrain (with a force constant of 2 kcal/mol·Å$^2$) was applied on the backbone of antibody. The SHAKE algorithm[45] was used to restrain the covalent bonds with hydrogen atoms, and the time step for the MD simulation was set to 2 fs. The long-range electrostatic interactions were treated by using the particle mesh Ewald (PME) algorithm,[46] and the nonbonded cutoff for the real-space interactions was set to 12 Å. Third, the last snapshots of the MD simulations were energy-minimized again using the same method described above for the energy-minimization of the free antibody structures without a ligand. Finally, the MMPBSA module of the AmberTools18 software was used to calculate the binding free energy of each antibody-ligand binding pose, leading to the identification of the antibody-ligand binding pose associated with the lowest binding free energy for each antibody-ligand complex.

With the lowest binding free energy pose for each antibody-ligand pair and the corresponding binding free energy determined, the antibody was selected with the lowest possible binding free energy (i.e. the highest possible binding affinity) with 6-MAM and with the best possible overall binding affinities with other heroin-related opioids as well as the desirable selectivity over naloxone and naltrexone.

Example 4: Antibody Humanization Design; Sequence Alignment and Modification

Humanization of the computationally selected antibody (i.e. murine antibody Ab13 in this study) was performed by using the X-ray crystal structure of Ab13 complexed with morphine[34] (PDB: 1Q0Y) from PDB database (rcsb.org/pdb/home/home.do) and the immunoinformatic modelling tools made available by the IMGT database.[38] Briefly, the variable heavy and light chain sequences (VH and VL) of the murine antibody were compared with human germline sequences using the IMGT/DomainGapAlign tools.[38] The top-ranked human germline sequence was used as the template. Murine antibody residues that differ from the human sequences on the surface area were replaced, excluding the residues near the binding pocket and anchor residues. Individual residues that are clearly not involved in the binding with the ligands in the murine antibody were changed to the corresponding residues of the human antibody. The image of the aligned sequences was created using the ESPript 3.0 software.[47]

Example 5: Antibody Humanization Design; MD Simulation and Final Sequence Selection The above-mentioned sequence modification based on the sequence alignment and simple structural modeling led to multiple (three) possible choices of the sequence of the humanized antibody, i.e. three possible humanized antibodies denoted as H1L1, H1L2, and H1L3. The initial structures of the antibodies (generated by using the PIGSpro software[39] as described above) were refined further by performing a series of energy minimization processes and restrained MD simulations in order to know which one of the three choices is most reasonable. Concerning the computational details, the Amber14SB force field[40] and the generalized Amber force field (gaff)[44] were used for the proteins and ligands, respectively. The TIP3P water molecules[48] were added as the solvent and the solute atoms were at least 10 Å away from the boundary of the water box using AmberTools18.[41] The counterions (i.e. Na$^+$ ions for murine antibodies or Cl$^-$ ions for humanized antibodies) were added to neutralize the system. The long-range electrostatic interactions were handled by the particle mesh Ewald (PME) algorithm,[46] and the nonbonded cutoff for the real-space interactions was set to 10 Å.

Energy minimization was performed using a hybrid protocol of 8000 steps of the steepest descent energy-minimization followed by the conjugate gradient energy-minimization until the convergence criterion (the root-mean-square of the energy gradient is less than $1.0 \times 10^{-4}$ kcal/mol·Å) was satisfied or the maximum of 2000 iteration steps was reached. During the energy minimization, a force constant of 100 kcal/mol·Å$^2$ was applied on the ligand and protein backbone atoms. Then the systems were heated up from 0 to 303.15 K linearly over a time period of 50 ps with the restraint (force constant of 10 kcal/mol·Å$^2$) on all heavy atoms in the NVT ensemble, followed by equilibrating for 325 ps with a Langevin thermostat[49] in the NPT (P=1 atm and T=303.15 K) ensemble by gradually decreasing the force constant from 10 to 0.2 kcal/mol·Å$^2$. Finally, the 5-ns production run was carried out with the PMEMD module of the Amber12 in the NPT (P=1 atm and T=303.15 K) ensemble. The SHAKE algorithm was used to restrain the covalent bonds with hydrogen atoms, and the time step was set to 2 fs, the snapshots were saved every 2 ps. The RMSD values were calculated by CPPTRAJ module of AmberTools18 using the energy-minimized conformations as the references.

Example 6: Plasmid Construction

To construct the chimeric antibody (UK6Mab01) and the (fully) humanized antibody (UK6Mab02), the amino acid sequences of heavy and light chains of variable domains of UK6Mab01 and UK6Mab02 were linked with human immunoglobulin heavy constant gamma 1 (IgG1, P01857, heavy chain) and human immunoglobulin kappa constant (IGKC, P01834, light chain), respectively.

The heavy and light chains were translated to human gene sequences by using the Backtranseq provided by the EMBL-EBI,[50] and the codon was optimized using the COOL.[51] The Kozak sequence and signal peptide sequences for heavy chain or light chain were added to optimized genes. Then the genes for heavy chain and light chain were linked by inserting an Internal Ribosome Entry Site (IRES) between them. The designed genes were synthesized by GeneArt (Invitrogen, Carlsbad, Calif.), followed by cloning the genes into the pCMV-MCS vector at the BamHI and SalI sites for the humanized antibody, and at the BamHI and XhoI sites for the chimeric antibody. The oligonucleotides were synthesized by the Eurofins Genomics (Louisville, Ky.), restriction enzymes and the KLD Enzyme Mix used for ligation were purchased from New England Biolabs (Ipswich, Mass.). The final plasmids used for transfection were verified by sequencing services provided by Eurofins Genomics (Louisville, Ky.).

Example 7: Protein Expression and Purification

CHO-S cells were grown under the condition of 37° C. and 8% $CO_2$ in a humidified atmosphere. The constructed expression vectors for the chimeric and humanized antibodies were transfected into CHO-S cells using Minis TransIT-PRO® Transfection Kit. 400 mL cells at the density of $2 \times 10^6$ cells/mL were transfected with 400 µg of expression vector and 400 µL of transfection reagent. Culture supernatants were harvested 5 days after transfection by centrifugation with 10000 rpm for 15 min at 4° C. Antibodies were purified with using a protein A resin (Mab Select SuRe™ ordered from GE Healthcare, Chicago, Ill.), as used previously.[52-54] Briefly, 5 mL resin was packed in a column, equilibrated with 20 mM Tris-Cl (pH=7.4), loaded the culture supernatants with flow rate of 1-2 mL/min, washed with wash buffer (20 mM Tris-Cl, 300 mM NaCl, pH=7.4), and eluted with elution buffer (50 mM citric acid, 300 mM NaCl, pH=4). Then the eluate was concentrated and stored in PB buffer. Purified proteins were analyzed by SDS-PAGE (Invitrogen, Carlsbad, Calif.).

Example 8: Antibody Binding Assays

The binding constant of the antibody with [H$^3$]-morphine were tested using liquid scintillation counting. Briefly, 2 nM [H$^3$]-morphine was incubated with different concentration of antibody at room temperature for 60 minutes. The total volume of mixture was 100 and pH was 7.4. Following filtration with EMD Millipore Amicon™ Ultra-0.5 Centrifugal Filter (30 kD) and EMD Millipore Amicon™ Ultra 0.5 mL vials, 50 µL of the filtrate was added to 3 mL of 3a70BTM complete counting cocktail (RPI Research Products, Mount Prospect, Ill.). After vortex, the radioactive value of the cocktail was read, the $K_d$ value was calculated using the GraphPad Prism 7 software.

The binding affinities of each antibody with other drugs were calculated from its binding constant with [H$^3$]-morphine ($K_d$) and $IC_{50}$ values against corresponding drugs, using the $IC_{50}$-to-$K_i$ converter software (umich.edu/~shaomengwanglab/software/calc_ki/index.html>. The $IC_{50}$ values of corresponding drugs were measured as follows. 100 µL of mixture (pH 7.4) containing 2 nM [H$^3$]-morphine, 20 or 60 nM of the antibody, and a varying concentration of drug was incubated at room temperature for 60 minutes. Then the mixture was filtered with EMD Millipore Amicon™ Ultra-0.5 Centrifugal Filter (30 kD) and EMD Millipore Amicon™ Ultra 0.5 mL Vials, 50 µL of the filtrate was transferred to 3 mL of 3a70BTM complete counting cocktail (RPI Research Products, Mount Prospect, Ill.), then the radioactive value of the cocktail was read, and the $IC_{50}$ value was calculated using the GraphPad Prism 7 software.

Example 9: Virtual Screening

According to the virtual screening of available antibodies, including all of those listed in Table 1 with known experimental binding affinity to any of the heroin-related opioids, 6-MAM may potentially bind with the 26 known antibodies listed in Table 1, but with different binding free energies ranging from −16.6 kcal/mol (for the most potent one, i.e. Ab13) to −2.0 kcal/mol (which represents a negligible binding affinity) (see Table 2). Hence, the binding free energies of these 26 antibodies with morphine, heroin, naloxone, and naltrexone were computationally estimated. All the calculated binding free energies are summarized in Table 2 in comparison with available experimental data.

TABLE 1

Variable region sequences of anti-morphine/6-MAM antibodies.

| Antibody | Original Name | HeavyChain | Heavy Chain SEQ ID NO: | LightChain | Light Chain SEQ ID NO: |
|---|---|---|---|---|---|
| Ab1 | MOR131 | QVQLQQSGPXLMEPGAS VKISCRASGYIFRTYWI EWIRERPGHGLEWIGEI LPGSGFTKYNEKFTGKA TITAEASSNTAYVQLNS LTSEDSAVYYCTRWGTG AGIIVMDFWGRGTSVTV SS | 13 | QPVVTQESALTTSPGE TVTLTCRSSTGAVTTS NYANWVQEKPDHLFTG LIGGTNNRAPGVPARF SGSLIGDKAALTITGA QIEDEALYFCVLWDSN RLVFGGGTKLTVL | 39 |
| Ab2 | MOR158 | QVQLQQPGXELVKPGXS VRLSCKATGYTFATYWM NWVKQRPGQGLEWIGEI NPSNGRTNYNERFQNKA SLTVDKSSSTAYMQLTS LTSEDSAVYFCARWVLR PLYALDYWGQGTSVTVS S | 14 | EIQVTQTTSSLSASLG DRVTISCRASQDIKNY LNWYQQKPDGTVKLLI YYTSTLHSGVPSRFSG SGSGTDYSLTIDNLEQ EDVATYFCQQGTTLPT WTFGGGXKVEIXRADA A | 40 |
| Ab3 | MOR180 | QVQLQQPGXELVKPGXS VRLSCKATGYTFATYWM NWVKXRPGQGLEWIGEI NPSDGRTNYNDRFKNKA TLTVDISSSTAYMQLSS LTSEDSAVYYCARWVLR PLYALDYWGQGTSVTVS S | 15 | EIQVTQTTSSLSASLG DRXT1XCRASQDIKNY XNWYQQKPDGTVKLLI YYTSSLHSGVPSRFSG SGSGTDYSLTISNLEQ EDVATYFCQQGTTLPT WTFGGGXKVEIKRADG A | 41 |
| Ab4 | MOR8 | EVKLVESGGGLVKPGGS LKLSCAASGFTFSSYVM SWVRQTPEKRLEWVASI SGGGTTYYPDSVKGRFT ISRDNARNILYLQMSSL RSEDAAMFYCAREDYYG SSYWYFDVWGAGXTVTV SS | 16 | DIVLTQSPASLAVSLG QRATISCKASQSVDYD GDSYMNWYQQKPGQPP XLLIYAASNLESGIPA RFSGSGSGTDFTLNIH PVEEEDAATYYCQRSN EDPFTFGSGTKLEIK | 42 |
| Ab5 | MOR33 | EVKLVESGXGXVKPGGS LKLSCAASGFTFSKYVM SWVRQTPERRLEWVASI GVSGITYFPDSVKGRFT ISRDNGRNVLYLQMSSL RSEDTAMYYCAREDYYG SRYWYFDVWGAGTXVTV SS | 17 | DIVLTQSPASLAVSLG QRATISCKASHSVDYD GDGYMNWYQQKPGQPP XLLIYAASNLESGIPA RFSGSGSGTDFTLNIH PVEEEDAATYYCQQSD GDPFPFGSGTKLEIK | 43 |
| Ab6 | MOR35 | EVKLVESGXXXVKPGGS LKLSCAASGFSFSRYVL SWVRQTPEKRLEWVASI SSGGTTYYPDSVKGRFT ISRDIARNILYLQLSSL RSDDTAMYYCAREDYYG GRYWYFDVWGAGXTVTV SS | 18 | DIVLTQSPASLAVSLG QRATISCKASQGVDFD GDAYMNWYQQKPGQPP XLLIYAASNLESGIPA RFSGSGSGTDFTLNIH PVEEEDAATYYCQQSD GDPFPFGSGTKLEIK | 44 |
| Ab7 | MOR44 | EVKLVESGAGVVKPGGS LKLSCEASGFSFSRYVM SWVRQTPEKRLEWVASI SSGGRTYYPGSEMGRFT ISRDSARNILYLQMSSL KSEDTAMFYCAREDYYG GRYWYFDVWGAGTTVTV SS | 19 | DIVLTQSPASLAVSLG QRATISCKASQSVDHD GNGYMNWYQQKPGQPP RLLIYAASNLEYGIPV RFSGSGSGTDFILNII IPVEEEDAATYYCQQS DGDPFPFGSGTKLEIK | 45 |

TABLE 1-continued

Variable region sequences of anti-morphine/6-MAM antibodies.

| Antibody | Original Name | HeavyChain | Heavy Chain SEQ ID NO: | LightChain | Light Chain SEQ ID NO: |
|---|---|---|---|---|---|
| Ab8 | MOR83 | EVICLVESGXGVVICPGGSLKLSCAASGFSFSRYMVSWVRQTPEKRLEWVASISSGGRTYYPGSETGRFTISRDSARNILYLQMSSLRSEDTAIFYCAREDYYGGRYWYFDVWGXGTXVTVSS | 20 | DIVLTQSPASLAVSLGQRATISCKASQSVDHDGNGYMNWYQQKPGQPPRLLIYAASNLESGIPVRFRGSGSGTDFILNIHPVEEEDAATYYCQQSDGDPFPFGSGTICLEIK | 46 |
| Ab9 | MOR76 | EVKLVESGXXXVKPGGSLKLSCAASGFSFSDYVMSWVRQTPEKRLEWVASISSGGRTYYPGSVKGRFTISRDDDRNILYLQMNSLRSEDTAMFYCAREDYYDSSYWYFDVWGTGTTVTVSS | 21 | DIVLTQSPASLAVSLGQRATISCKASQSVDFDGDNYMNWYQQKPGQSPICLLIYAASNLQSGIPARFSGSGSGTDFTLNIEPVEEEXAATYYCQRSNEDPFTFGSGTICLEIK | 47 |
| Ab10 | MOR39 | QVQLQQSGPXLMKPGXSVKISCKATGYTERTYWIEWIICERPGHGLEWIGEILPGSGITKYXEKFKGKAIITADTSSNTAYVQLSSLTSEDSAVYYCTRWGTGTGHVMDYWGQGTSVTVSS | 22 | QAVVTQESALTTSPGETVTLTCRSSTGAVTTSNYANWVQEKPDHLFTGLIGGTDNRAPGVPARFSGSLIGDKAALTITGAQTEDEAVYFCVLWDSNRLVFGGGTKLTVL | 48 |
| Ab11 | 11C7 | EVNLLESGGGLVQPGGSLKVSCAASGFDFSRFWMSWVR.QAPGKGLEWIGEINPSSNTINYTPSLICERFIISRDNAICNTLYLQMSKVRPEDTGLYYCAMTKSVYNYGSHYYYFDVWGAGTITVTSS | 23 | AVVTQESILTTSPGETVTLTCRSSTGAVTTSNYANWVQQKPDHLFTSLIGGISNRVPGVPARFSGSLIGDKVALTIIGTQTEDEAIYFCALWYSNHLVFGGGTKLTVL | 49 |
| Ab12 | 12D4 | QVHLQQSGAELMKPGSSVKISCKTTGYTFSNYWIEWIKERPGHGLVWIGEILPGTGRTFYSENFKVICATFITDTSSNTAYLQLSSLTSEDSAVYYCARWFRDLYGVDYWGQGTSVTVSS | 24 | AVVTQESILTTSPGETVTLTCRSSTGAVTTSYANWVQEKPDHLFTGLIGGTNNRAPGVPARFSGSLIGDKAALTITGAQTEDEAINTCALWYSNHLVFGGGTKLTVL | 50 |
| Ab13 | 9B1 | EVQLQQSGAELMKPGASVKISCKATGYIFSSYWIEWVKQFRPG1TGLEWIGEILPGSGDTIFNEICFKGICATFTADTSSNTAYMQLSSLTSEDSAVYYCARWVLDYYGMDYWGQGTSLTVSS | 15 | DAVVTQESALTTSPGETVTLTCRSSTGAVTTSNYANWVQEKPDHLFTGLIGGTNNRAPGVPARFSGSLIGDICAALTITGAQTEDEAIYFCALWSNNKLVEGGGTKLTVL | 51 |
| Ab14 | 10C3 | MDFGLIFF1VALLKGVQCEVICLLESGGGLVQPGGSLKLSCAASGFDFSRYWILVRQAPGKGLEWIGEINPIISTTIFYTPSLMDKFIISRDNAKNTLYLQMTKVRSEDTALYYCARWGDKYLFDFIWGQGTTLTVSS | 26 | AVVTQESALTTSPGETVTLTCRSSTGAVTTSNYANWVQEKPDHLFTGLIGGTNNRAPGVPARFSGSLIGDKAALTITGAQTEDEAIYFCSLWYSNHLVEGGGTKLTVL | 52 |
| Ab15 | 368-21 | EVICPLESGGGLVQPGGSLICLSCAASGEDFSRYWMSWVRQAPGKGLEWIGEIHPDSSTIFYTPSLICDICFIISRDNAICETLYLQMTKVRSEDTALYITARWSLRGYYFDYWGQGTTLTVSS | 27 | QAVVTQESAL17SPGETVTLTCRSSTGAVTTSNYATWVQEKPDHLFTGLIGVTNYGPPGVPSRFSGSLIGDKAALTITGAQTEEEAMYFCALWDSNHPNTGGGTKLTVL | 53 |

TABLE 1-continued

Variable region sequences of anti-morphine/6-MAM antibodies.

| Antibody | Original Name | HeavyChain | Heavy Chain SEQ ID NO: | LightChain | Light Chain SEQ ID NO: |
|---|---|---|---|---|---|
| Ab16 | 402-10 | EVKPLESGGGLVQPCGS LKLSCAASGFDFSRYWM SWVRQAPRKRLEWIGEI NPDSSTITYTPSLICDI CFIISRDNAKNTLYLQM SKVRSEDTALYYCASWY GLRLSYEDVWGAGTTVT VSS | 28 | QAVVTQESALTTSPGE TVTLTCRSSTGAVTTS NYATWVQEKPDHLFTG LIGVTNYGPPGVPSRF SGSLIGDKAALTITGA QTEEEAMYFCALWDSN LIPVEGGGTKLTVL | 54 |
| Ab17 | 6-MAM-214 | EVQLVESGGGLVQPGRS LRLSCAASGFSFGDYAI HMVRQAPGKGLEWVSGI SWDSYTTGYADSVKGRF TVSRDNAKNSLYLQMNS LRPEDTAVYYCAKAPSP RRVIIEYFDSDYWGQGT SLTVSS | 29 | QSALTQPASVSGAPGQ TVSISCTGWSSNIGAG YDVHWYQQLPGTAPKL LISHNTNRPSGVPDRF SGSKSGTSASLAITGL QAEDEADYYCQSYDST LGVVVEGGGTICLTVL | 55 |
| Ab18 | 6-MAM-20 | EVQLVESGGGLVQPGRS LRLSCAASGFSFGDYAI HMVRQAPGKGLEWVSGI SWDSYTTGYADSVKGRF TVSRDNAICNSLYLQMN SLRPEDTAVYYCAKAPS PRRVIIEYFDSDYWGQG TSLTVSS | 30 | QSALTQPASVSGAPGQ RVTISCTGSSSNIGAG YAVHWYQQLPGTAPKL LIYDDNNRPSGVPDRF SGSKSDTSASLAITGL QADDEADYYCQSYDSS LSGVFGTGTKLTVL | 56 |
| Ab19 | 6-MAM-219 | EVQLVESGGGLVQPGRS LRLSCAASGFSFGDYAR IMVRQAPGKGLEWVSGI SWDSYTTGYADSVKGRF TVSRDNAICNSLYLQMN SLRPEDTAVYYCAKAPS PRRVIIEYFDSDYWGGT SLTVSS | 31 | QSVLTQPPSVSGAPGQ RVTISCTGSSSNIGAG YDVHWYQQLPGTAPKL LIYGNSNRPSGVPDRF SGSKSGTSASLAITGL QAEDEADYYCQSYDSS LRGVVFGGGTKLTVL | 57 |
| Ab20 | 6-MAM-102 | EVQLVESGGGLVQPGRS LRLSCAASGFSTGDYAI HMVRQAPGKGLEWVSGI SWDSYTTGYADSVKGRF TVSRDNAKNSLYLQMNS LRPEDTAVYYCAKAPSP RRVHEYFDSDYWGQGTS LTVSS | 32 | QSALTQPASVSGAPGQ RVTMSCTGSSSNIGAG YDVHWYQQLPGTAPKL LIFGNTNRPSGVPDRF SASKSGTSASLAITGL QAEDEADYYCQSYDNS LSGVVFGGGTKLTVL | 58 |
| Ab21 | 6-MAM-103 | EVQLVESGGGLVQPGRS LRLSCAASGFSFGDYAI HMVRQAPGKGLEWVSGI SWDSYTITGYADSVKGR FTVSRDNAICNSLYLQM NSLRPEDTAVYYCAKAP SPRRVIIENTDSDYWGQ GTSLTVSS | 33 | QSALTQPASVSGAPGQ RVTISCTGSSSNIGAG YDVHWYQQLPGTAPKL LIYGNSNRPSGVPDRF SGSKSGTSASLAITGL QAEDEADYYCQSYDSS LSGVVFGGGTKLTVL | 59 |
| Ab22 | 6-MAM-108 | EVQLVESGGGLVQPGRS LRLSCAASGFSTGDYAI HMVRQAPGKGLEWVSGI SWDSYTTGYADSVKGRF FVSRDNAKNSLYLQMNS LRPEDTAVYYCAKAPSP RRVIIEYFDSDYWGQGT SLTVSS | 34 | QSVLTQPPSVSGAPGQ RVTISCTGSSSNIGAG YDVHWYQQLPGTAPKL LWGNSNRPSGVPDRFS GSKSGTSASLAITGLQ AEDEADYYCQSYDSSL SGVVFGGGTKLTVL | 60 |
| Ab23 | 6-MAM-49 | EVQLVESGGGLVQPGRS LRLSCAASGFTFGDYAI IMVRQAPGKGLEWVAG ISWDSYTTGYADSVKGR FTVSRDNAKNSLYLQMN SLRPEDTAVYYCAICAP SPRRVIIENTQYDYWGQ GTSLTVSS | 35 | QSALTQPASVSGAPGQ TVSISCTGWSSNIGAG YDVHWYQQLPGTAPKL LISIINTNRPSGVPDR FSGSKSGTSASLAITG LQAEDEADYYCQSYDS TLGVVEGGGTKLTVL | 61 |

TABLE 1-continued

Variable region sequences of anti-morphine/6-MAM antibodies.

| Antibody | Original Name | HeavyChain | Heavy Chain SEQ ID NO: | LightChain | Light Chain SEQ ID NO: |
|---|---|---|---|---|---|
| Ab24 | 6-MAM-120 | EVQLVESGGGLVQPGRSLRLSCAASGFTFGDYAIHMVRQAPGKGLEWVAGISWDSYTTGYADSVKGRFTVSRDNAKNSLYLQMNSLRPEDTAVYYCMCAPSPRRVIIEYFQYDYWGQGTSLTVSS | 36 | QSALTQPASVSGAPGQRVTISCTGSSSNIGAGYDVHWYQQLPGTAPKLLIYGNSNRPSGVPDRFSGSKSGTSASLAITGLQAEDEADYYCQSYDSSLSGVVFGGGTKLTVL | 62 |
| Ab25 | M86 | DVKINESGGGINKPGGSLKLSCAASGETSSSYAMSWVRQSPETCRLEWVASTSSGGSTYYPDSVKGRFTTSRDNARNNLYLQMSSLRSEDTAMYYCVREDYHGSSYWYFDVWGAGTIVTVSS | 37 | DIVLTQSPARLAVSLGQRATISCKASQSVDYDGDSYMNWYQQKPGQPPICLLIYAASNLESGIPARFSGSGSIDFTLNIHPVEEEDAATYYCQQSNEDPWTFGGGTKLEIKR | 63 |
| Ab26 | M3G | QVQLQQSGPELMKPGASVKISCKATGYTFSSHWIEWVKQRPGHGLEWTGEILPGSGSTKYNEKFKGKATFTADTSSNTVYMQLSSLTSEDSAVYHCARWSQVI1VMDYWGQGTSLTVSS | 38 | ESALTTSPGETVTLTCRSSTGAVTTSNYANWVQEKPDHLFTGLIGGTNNRAPGVPARFSGSLIGDKAALTITGAQTEDEANFCVLWYSNEILVEGGGTCKLTVL | 64 |

TABLE 2

The predicted binding free energies and the activities of known anti-morphine antibodies against morphine, 6-MAM, heroin, naloxone, and naltrexone.

| Antibody | Original Name | MMPBSA (kcal/mol)/ Activities (nM)$^a$ | Morphine | 6-MAM | Heroin | Naloxone | Naltrexone |
|---|---|---|---|---|---|---|---|
| Ab1 | MOR131 | MMPBSA | −17.6 | −11.6 | −10.8 | −14.4 | −4.1 |
| | | Activities[1] | 0.022 ($K_d$) | nd$^b$ | nd | 144.9 ($K_d$) | nd |
| Ab2 | MOR158 | MMPBSA | −10.2 | −11.6 | −4.5 | −12.2 | −11.5 |
| | | Activities[1] | 0.118 ($K_d$) | nd | nd | 34.6 ($K_d$) | nd |
| Ab3 | MOR180 | MMPBSA | −11.7 | −12.4 | −20 | −12.5 | −15.6 |
| | | Activities[1] | 0.25 ($K_d$) | nd | nd | 67.6 ($K_d$) | nd |
| Ab4 | MOR8 | MMPBSA | −15.7 | −14.8 | −16.4 | −10.1 | −15.6 |
| | | Activities[1] | 0.143 ($K_d$) | nd | nd | 142.9 ($K_d$) | nd |
| Ab5 | MOR33 | MMPBSA | −15.4 | −13.6 | −13.4 | −8.1 | −11.5 |
| | | Activities[1] | 0.189 ($K_d$) | nd | nd | 145.1 ($K_d$) | nd |
| Ab6 | MOR35 | MMPBSA | −15.7 | −14.7 | −19.1 | −7.6 | −11.9 |
| | | Activities[1] | 0.185 ($K_d$) | nd | nd | 115.7 ($K_d$) | nd |
| Ab7 | MOR44 | MMPBSA | −12.7 | −11.4 | −14.2 | −9.7 | −15.8 |
| | | Activities[1] | 0.119 ($K_d$) | nd | nd | 44.82 ($K_d$) | nd |
| Ab8 | MOR83 | MMPBSA | −10.2 | −8.5 | −12.4 | −12.7 | −10.8 |
| | | Activities[1] | 0.103 ($K_d$) | nd | nd | 44.82 ($K_d$) | nd |
| Ab9 | MOR76 | MMPBSA | −12.9 | −15.1 | −17.0 | −12.5 | −18.8 |
| | | Activities[1] | 0.063 ($K_d$) | nd | nd | 32.89 ($K_d$) | nd |
| Ab10 | MOR39 | MMPBSA | −15.7 | −10.6 | −17.7 | −3.8 | −16.1 |
| | | Activities[1] | 2.174 ($K_d$) | nd | nd | 48309 ($K_d$) | nd |
| Ab11 | 11C7 | MMPBSA | −17.8 | −2.0 | −10.2 | −16.8 | −5.4 |
| | | Activities[2] | 16.17 ($K_d$) | nd | nd | nd | nd |
| Ab12 | 12D4 | MMPBSA | −12.1 | −10.5 | −9.9 | −4.3 | −4.8 |
| | | Activities[2] | 13.64 ($K_d$) | nd | nd | >10000 ($K_d$) | nd |
| Ab13 | 9B1 | MMPBSA | −15.1 | −15.6 | −16.6 | −1.8 | −3.2 |
| | | Activities[3] | 1 ($K_d$) | nd | nd | nd | nd |
| Ab14 | 10C3 | MMPBSA | −15.5 | −12.9 | −15.0 | −9.7 | −14.7 |
| | | Activities[2] | 53.83 ($K_d$) | nd | nd | 5105 ($K_d$) | nd |
| Ab15 | 368-21 | MMPBSA | −17.8 | −11.9 | −15.2 | −3.0 | −10.2 |
| | | Activities[4] | 3.1 ($K_d$) | nd | nd | 81 ($IC_{50}$) | 310 ($IC_{50}$) |
| Ab16 | 402-10 | MMPBSA | −13.6 | −15.4 | −7.3 | −5.3 | −16.5 |
| | | Activities[4] | 3.5 ($K_d$) | nd | nd | 100 ($IC_{50}$) | nd |
| Ab17 | 6-MAM-214 | MMPBSA | −5.0 | −8.7 | −5.6 | −13.3 | −1.7 |
| | | Activities[3] | >10000 ($K_d$) | 300 ($K_d$) | nd | nd | nd |

TABLE 2-continued

The predicted binding free energies and the activities of known anti-morphine antibodies against morphine, 6-MAM, heroin, naloxone, and naltrexone.

| Antibody | Original Name | MMPBSA (kcal/mol)/ Activities (nM)[a] | Morphine | 6-MAM | Heroin | Naloxone | Naltrexone |
|---|---|---|---|---|---|---|---|
| Ab18 | 6-MAM-20 | MMPBSA | −9.2 | −9.8 | −9.9 | −15.8 | −10.6 |
|  |  | Activities | nd | nd | nd | nd | nd |
| Ab19 | 6-MAM-219 | MMPBSA | −7.9 | −7.1 | −6.8 | −17 | −13.6 |
|  |  | Activities[5] | 10000 ($K_d$) | 160 ($K_d$) | nd | nd | nd |
| Ab20 | 6-MAM-102 | MMPBSA | −3.3 | −8.1 | −8.5 | −6.1 | −8.5 |
|  |  | Activities[3] | >10000 ($K_d$) | 170 ($K_d$) | nd | nd | nd |
| Ab21 | 6-MAM-103 | MMPBSA | −8.0 | −9.2 | −11.1 | −14.1 | −14.9 |
|  |  | Activities[5] | >10000 ($K_d$) | 100 ($K_d$) | nd | nd | nd |
| Ab22 | 6-MAM-108 | MMPBSA | −2.9 | −6.9 | −8.6 | −15.6 | −13.4 |
|  |  | Activities[5] | >10000 ($K_d$) | 170 ($K_d$) | nd | nd | nd |
| Ab23 | 6-MAM-49 | MMPBSA | −6.9 | −6.4 | −9.6 | −13.7 | −5.6 |
|  |  | Activities[5] | nd | nd | nd | nd | nd |
| Ab24 | 6-MAM-120 | MMPBSA | −10.9 | −6.7 | −16.0 | −4.6 | −4.8 |
|  |  | Activities[5] | >10000 ($K_d$) | 250 ($K_d$) | nd | nd | nd |
| Ab25 | M86 | MMPBSA | −11.5 | −11.2 | −15.1 | −14.9 | −20.3 |
|  |  | Activities[6] | 12.6 ($K_d$) | nd | 5.2 ($K_d$) | nd | nd |
| Ab26 | M3G | MMPBSA | −13.2 | −12.4 | −7.5 | −8.7 | −15.3 |
|  |  | Activities | nd | nd | nd | nd | nd |

[a]The experimental activity data were collected from the references cited. Reported $K_a$ and $IC_{50}$ values were coverted to the corresponding $K_d$ and $K_i$, respectively.
[b]nd (not determined) means no available experimental data.
[1]Jun-ichi, S., et al. (1993).
[2]Glasel, J.A., et al. (1983).
[3]Pozharski, E., et al. (2004).
[4]Kussie, P.H., et al. (1991).
[5]Moghaddam, A., et al. (2003).
[6]Matsukizono, M., et al. (2013).

Interestingly, for many of these antibodies listed in Table 2, experimental binding free energies (converted from the previously reported $K_d$, $K_i$, or $IC_{50}$ values according to the well-known thermodynamic equation) have already been known for their binding with morphine and naloxone. According to the experimental binding affinities summarized in Table 2, the most potent anti-morphine antibodies (Ab1 to 9), Ab15, and Ab16, can also potently bind to naloxone with nanomolar $K_d$ or $IC_{50}$ values (ranging from 33 nM to 145 nM). Ab15 even can potently bind with naltrexone ($IC_{50}$=310 nM). A therapeutic antibody capable of binding with naloxone or naltrexone would be problematic because it would block the favorable pharmacologic action of naloxone (the currently available therapeutic agent for opioid overdose treatment) or naltrexone (the currently available therapeutic agent for opioid dependence treatment). For this reason, these potent anti-morphine antibodies would not be suitable for consideration as the desirable therapeutic candidates. Nevertheless, the available experimental data for enough number of antibodies binding with morphine and naloxone allowed us to analyze the potential correction between and computational and experimental data and, thus, validate the computational protocol. In comparison, only six antibodies have experimental data available for their binding with 6-MAM, with a very narrow range of the $K_d$ values (100 to 300 nM) that had limited the correlation analysis for 6-MAM before further experimental data was obtained to expand the range (see below).

Figure 1:
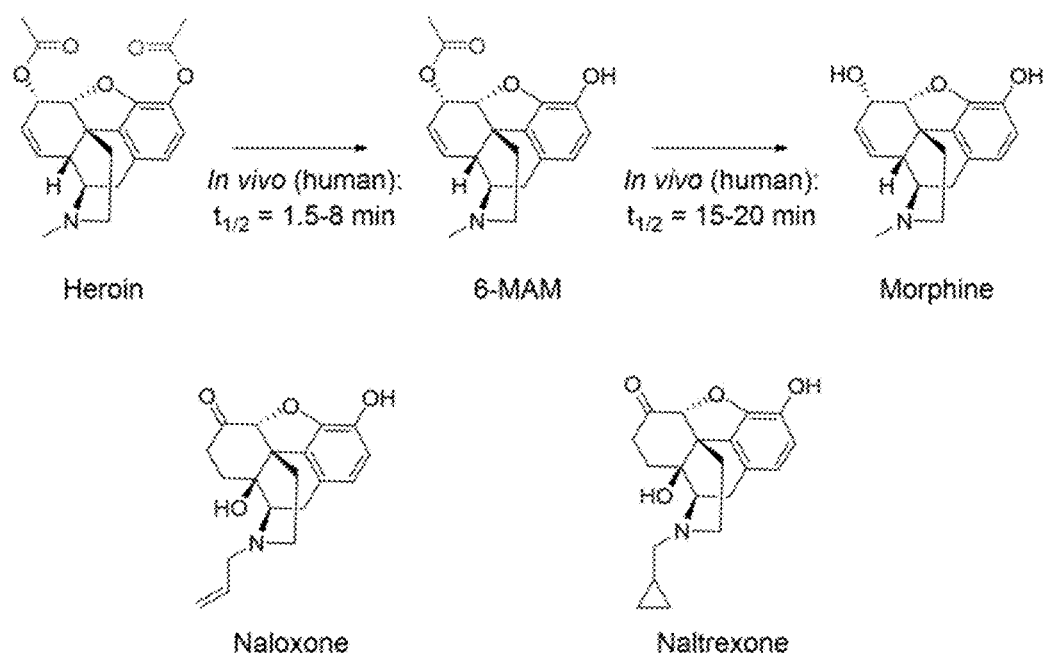
FIG. 1. Molecular structures of heroin and its key metabolites, as well as FDA-approved prescription drugs naloxone and naltrexone for treatment of heroin overdose and dependence, respectively.
Figure 2A:
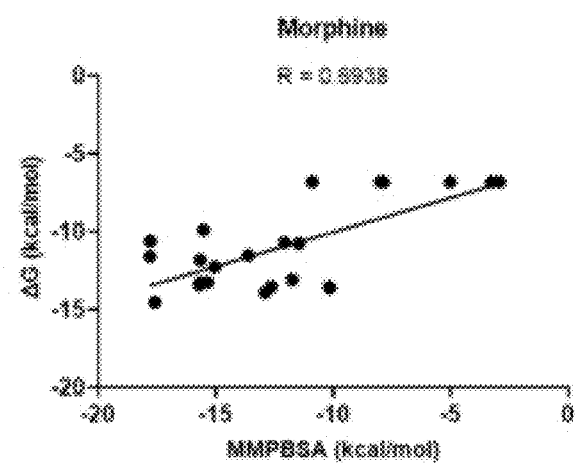
FIGS. 2A and 2B. The linear correlation between the predicted binding free energies with the experimentally derived binding free energies (converted from the reported binding affinity data listed in Table 2 by using the well-known thermodynamic equation) for morphine (FIG. 2A) and naloxone (FIG. 2B).
Figure 2B:
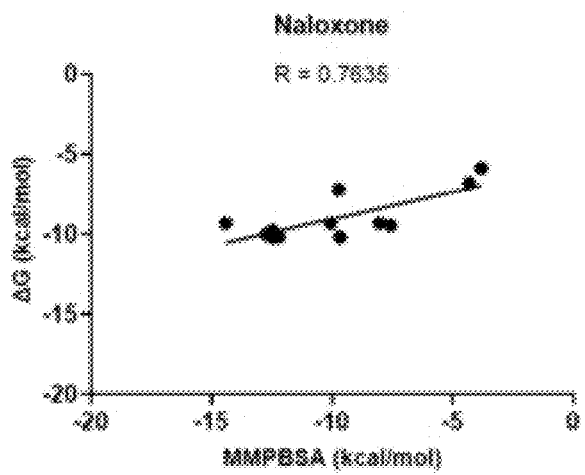

As showed in FIG. 2, the predicted binding free energies correlate with the corresponding experimental data very well, with the correlation coefficient being 0.6938 and 0.7635 for morphine and naloxone, respectively. The good correlation between the computational and experimental data suggests that the computational protocol for predicting the binding structures and relative binding free energies is reasonable. Thus, the most potent antibody for 6-MAM could be confidently predicted based on the computational data obtained from the use of the same computational protocol.

Within all antibodies listed Table 2, Ab13 was predicted to have the lowest binding free energy (−15.6 kcal/mol) with 6-MAM; the lowest binding free energy means the highest binding affinity. Ab13 was also predicted to have high binding affinities with morphine and heroin (corresponding to the calculated binding free energies of −15.1 and −16.6 kcal/mol, respectively). Interestingly, Ab13 was predicted to have the highest binding free energy (i.e. the lowest binding affinity) with naloxone and naltrexone (corresponding to the calculated binding free energies of −1.8 and −3.2 kcal/mol, respectively). In other words, Ab13 was predicted to be the most promising antibody capable of potently binding with 6-MAM, morphine, and heroin without significant binding affinity with naloxone and naltrexone.

Example 10: Binding Modes of Ab13 with Heroin-Related Opioids

To identify the key residues of Ab13 for the binding with 6-MAM, morphine, and heroin, the X-ray crystal structure of the complex of Ab13 with morphine was taken from the RC SB Protein Data Bank, together with the predicted binding structures of 6-MAM and heroin, were analyzed and presented in FIG. 3. As shown in FIG. 3A, I59, W33, L101, and Y104 of the heavy chain and Y34, W93, and L98 of the light chain form a hydrophobic pocket and encase 6-MAM. E50 of the heavy chain has strong ionic interactions with the cationic nitrogen of 6-MAM, and this cationic nitrogen also forms π-cation interactions with W93 of the light chain and W99 of the heavy chain. The 6-acetyl group of 6-MAM forms a hydrogen bond with the W33 side chain of the heavy chain.

In addition, as shown in FIGS. 3A and 3B, the methyl substituent on the nitrogen of 6-MAM has favorable Van der Waals interaction with W99 side chain of the heavy chain and L98 side chain of the light chain; replacing this methyl group with allyl group (naloxone) or cyclopropylmethyl group (naltrexone) would lead to clash with the W99 and L98 residues, which is likely the reason why both naloxone and naltrexone were predicted to have negligible binding affinity with Ab13. Compared to 6-MAM, morphine and heroin employ a similar binding mode in binding with Ab13 (see FIGS. 3C and 3D). Besides the interactions of 6-MAM with Ab13, the 3-acetyl group of heroin has favorable hydrophobic interactions with L101 and Y104 side chains of the heavy chain, whereas morphine has lost the hydrogen bond between 6-MAM with W33 of the heavy chain. These binding features further explain the computational insights from the above-mentioned binding free energy calculations that Ab13 is expected to have favorable binding with 6-MAM, heroin, and morphine without favorable binding with naloxone and naltrexone.

Example 11: Ab13 Humanization Design

Ab13 was acquired from mouse by using the hybridoma technique.[34] To make use of this antibody for future use in human, Ab13 must be humanized to reduce immune response. Currently, many methods have been used in antibody humanization, the most wildly used methods are complementarity determining regions (CDRs) graft and antibody resurfacing.[55] As CDRs graft change the framework regions (FRs) of the humanized antibody, certain key residues in FRs of Ab13 play an important role in binding with 6-MAM, heroin, and morphine according to the modelled binding structures (see FIG. 3). These critical residues should remain unchanged during the process of humanization. Therefore, the Ab13 humanization design was carried out by using an MD simulation and bioinformatics analysis-based resurfacing humanization method.

Initially, the amino-acid sequences of the variable domains of the heavy (VH) and light (VL) chains of Ab13 were analyzed using the IMGT/DomainGapAlign tools,[38] and the closest human germline V and J genes were identified. As shown in FIG. 4, the top-ranked human germline sequences for VH are IGHV1-46*01, IGHV1-69*02, and IGHJ4*01, and the top-ranked human germline sequences for VL are IGLV7-46*01, IGLV8-61*01, and IGLJ3*01. In order to maintain the binding pocket for 6-MAM, heroin, and morphine, murine amino-acid residues within the binding pocket were retained. The framework residues that are buried in the structure were considered potentially important for maintaining the conformation of the variable region and, thus, were also retained in the humanized antibody. Other murine residues that differ from the human counterpart were replaced. Following these criteria, one variable heavy chain (H1) and three possible light chains (L1, L2, and L3) of the humanized antibody were proposed (see FIG. 4).

Figure 6:
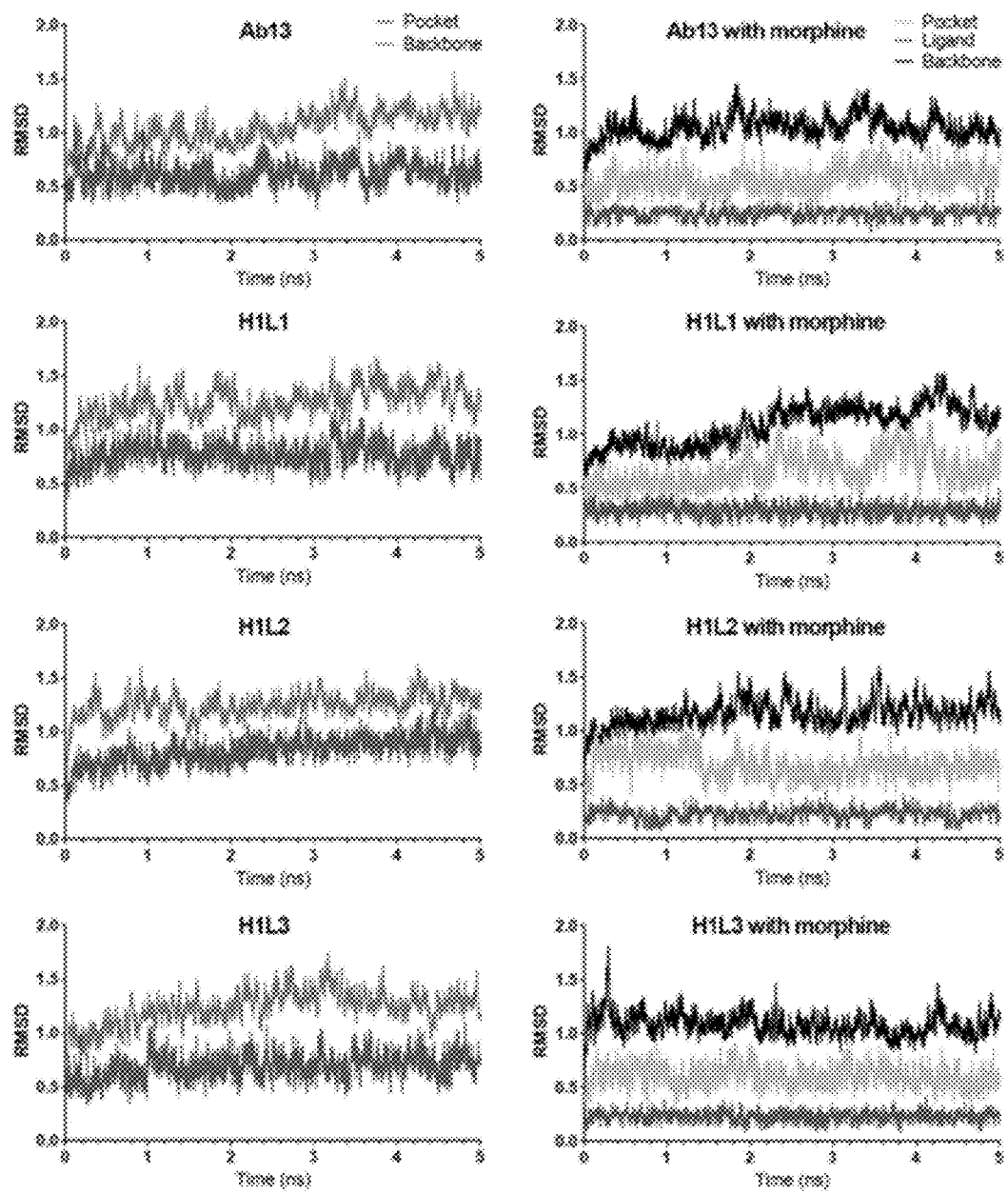
FIG. 6. MD simulations and time-dependent root-mean-square deviation (RMSD) values for the structures of Ab13, the humanized antibodies, and their complexes with morphine. The curves indicate the RMSD fluctuation in the MD-simulated structures. The RMSD values of the pocket residues were calculated for the alpha- and beta-carbons of the amino acids. The RMSD values of the back bones were calculated with peptide bond atoms of the antibodies.

Further, for assessment of the structural stability of the humanized antibody within the above three possible choices of the humanized antibody, MD simulations were carried out to examine the fluctuation of the residues in the binding pocket and the backbone atoms of the three possible humanized antibodies (denoted as H1L1, H1L2, and H1L3). For comparison, MD simulations were also performed on the original structures of Ab13 and its complex with morphine, and the time-dependent root-mean-square deviations (RMSDs) for all the simulated structures are provided in FIG. 6. Based on the time-dependent RMSD data (FIG. 6), the structures of Ab13 and its complex with morphine were stable during the MD simulations, as the RMSDs of the pocket residues and backbone atoms were only ~0.5 and ~1.1 Å, respectively. The ligand (morphine) in the complex had a very low fluctuation, with the RMSD being ~0.25 during the simulation, showing the stability of the complex.

In comparison, the pocket residues of H1L1 were stable during the MD simulation on H1L1 without morphine bound, but less stable during the MD simulation on the H1L1-morphine complex. On the contrary, the pocket residues of H1L2 were less stable during the MD simulation on H1L2 without morphine bound, as the RMSDs continually increased during the simulation, although the simulated H1L2-morphine complex structure was relatively more stable. Within the three humanized antibodies, H1L3 has the most stable structure, as reflected by the low RMSDs (for both the pocket residues and backbone atoms, as well as morphine bound) that were stable during the MD simulations on H1L3 with or without morphine bound. So, H1L3 was the final choice of the fully humanized antibody.

Besides, for the purpose of functional comparison, a chimera antibody (a partially humanized antibody) was also designed, in which only the Fc part of the mouse Ab13 was replaced by the Fc of human IgG-1. Such a chimera antibody was expected to have the same functions with the mouse Ab13. For convenience, the chimera antibody and the fully humanized antibody (H1L3) are denoted as UK6Mab01 and UK6Mab02, respectively, in the discussion below.

Example 12: Experimental Validation of the Designed Antibodies

Figure 5A:
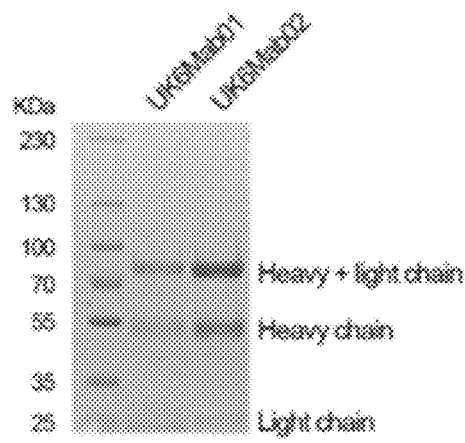

To prepare the designed antibodies UK6Mab01 and UK6Mab02, the sequences of heavy and light chains were assembled with human immunoglobulin heavy constant gamma 1 (IgG1, P01857) and human immunoglobulin kappa constant (IGKC, P01834), respectively. The use of internal ribosome entry site (IRES) allowed for the co-expression of a light chain and its corresponding heavy chain under the control of the same promoter. Both UK6Mab01 and UK6Mab02 proteins were expressed in the CHO-S cells and purified. A major band of approximately 75 kDa was observed, corresponding to the integrity of heavy and light chains. Two other major bands with molecular masses of approximately 50 kDa (heavy chain) and 25 kDa (light chain) were also observed (FIG. 5A).

Figure 5B:
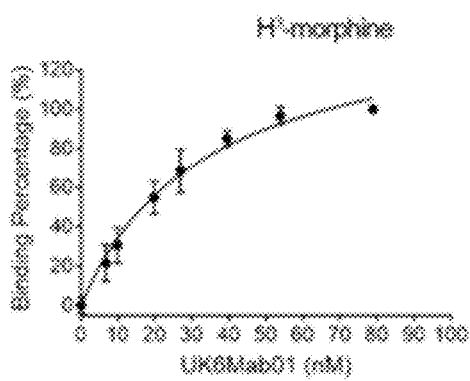
Figure 5C:
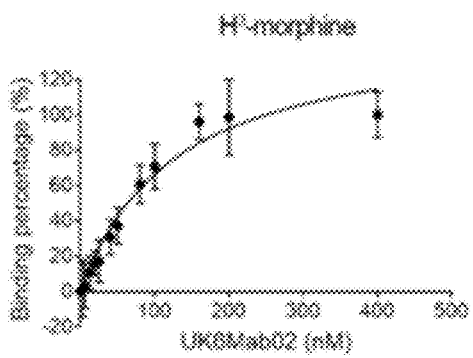
Figures 5D, 5E, 5F:
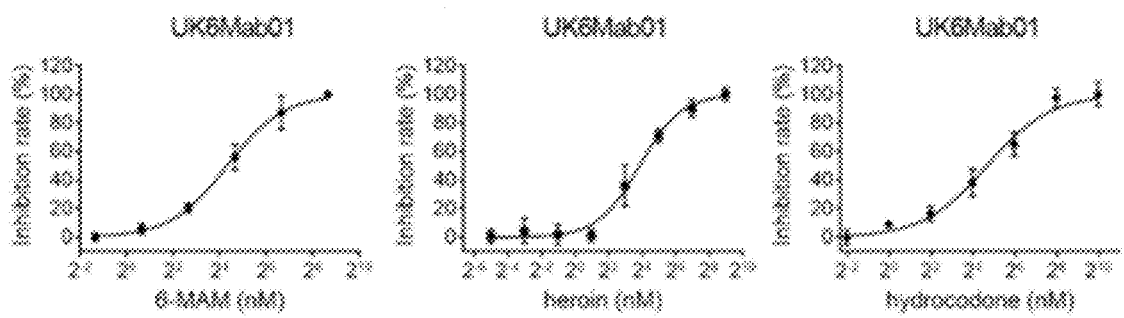

The binding affinities of UK6Mab01 and the UK6Mab02 with various ligands were assessed by the liquid scintillation counting method. Both the UK6Mab01 and UK6Mab02 were able to potently bind to morphine with a $K_d$ value of 33.7 nM (FIG. 5B) and 127 nM (FIG. 5C), respectively (Table 3). As expected, both UK6Mab01 and UK6Mab02 can also potently bind with 6-MAM and heroin. Specifically, UK6Mab01 has a high binding affinity to 6-MAM ($K_d$=4.8 nM) (FIG. 5D) and heroin ($K_d$=1.3 nM) (FIG. 5E). UK6Mab02 also has a high affinity to 6-MAM and heroin, with $K_d$=11.9 nM (FIG. 5G) and 11.8 nM (FIG. 5H), respectively. The binding affinities of the fully humanized antibody UK6Mab02 with these heroin-related opioids are only slightly weaker than the partially humanized chimera antibody UK6Mab01.

TABLE 3

Experimental binding affinities of UK6Mab01, UK6Mab02, and 9B1 with multiple drugs.

| Drugs | $K_d$ (nM) [a] UK6Mab01 | UK6Mab02 | 9B1 [a] |
|---|---|---|---|
| morphine | 33.7 | 127 | 1 |
| 6-MAM | 4.8 | 11.9 | nd [b] |
| heroin | 1.3 | 11.8 | nd |
| hydrocodone | 8.2 | 39.3 | nd |
| meperidine | 8,890 | 15,700 | nd |
| oxycodone | 2,670 | 6,910 | nd |
| fentanyl | 32,900 | 9,730 | nd |
| naloxone | >10,000 | >10,000 | nd |
| naltrexone | >10,000 | >10,000 | nd |

[a] Data from reference 33.
[b] nd (not determined) means no available experimental data.

In addition, UK6Mab01 and UK6Mab02 were examined to determine whether they can potently bind to other drugs including naloxone, naltrexone, hydrocodone, meperidine, oxycodone, methadone, amethaphetamine, ketamine, cocaine, and fentanyl (FIG. 5J). According to the initial screening at 10 µM, most of these drugs including naloxone and naltrexone did not show significant binding affinities with UK6Mab01 and UK6Mab02. However, both UK6Mab01 and UK6Mab02 can potently bind to hydrocodone (a widely abused prescription opioid), with $K_d$=8.2 nM (FIG. 5F) and 39.3 nM (FIG. 5I), respectively. Besides, UK6Mab01 and UK6Mab02 also showed relatively lower binding affinities with hydrocodone, oxycodone, and fentanyl (see Table 3 for a summary of the experimental binding affinities). The experimentally measured high binding affinities of the humanized antibodies with these heroin-related opioids without significant binding with naloxone and naltrexone are consistent with the computational predictions from the structure-based virtual screening.

Further, with the newly obtained binding affinity of 6-MAM with UK6Mab01, the computationally predicted binding free energies with 6-MAM were also able to be shown to excellently correlate with the corresponding experimental data (FIG. 5K), with a correlation coefficient of 0.9468.

The systematic structure-based virtual screening of available monoclonal antibodies and computational design of antibody humanization have led to discovery of promising antibodies, including the partially humanized antibody UK6Mab01 and the fully humanized antibody UK6Mab02, that can potently bind to multiple addictive opioids (including 6-MAM, morphine, heroin, and hydrocodone) without significant binding with currently available opioid overdose/dependence treatment agents naloxone and naltrexone. Specific for UK6Mab01, it was determined that $K_d$=4.8 nM for 6-MAM, 1.3 nM for heroin, 33.7 nM for morphine, 8.2 nM for hydrocodone, and 2.7-32.9 µM for oxycodone, meperidine, and fentanyl, without significant binding affinity to other drugs tested. For UK6Mab02, it was determined that $K_d$=11.9 nM for 6-MAM, 11.8 nM for heroin, 127 nM for morphine, 39.3 nM for hydrocodone, and 6.9-15.7 µM for oxycodone, fentanyl, and meperidine, without significant binding affinity to other drugs tested. The fully humanized antibody are contemplated for use in treatment of OUDs.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Tuttle, I., America's Heroin Crisis Was Birthed by the Law of Unintended Consequences (nationalreview.com/article/430274/heroin-prescription-painkillers-America-growing-crisis). Jan. 25, 2016 3:23 PM (last seen: Jan. 27, 2018).
2. Meijler, M. M.; Kaufmann, G. F.; Qi, L.; Mee, J. M.; Coyle, A. R.; Moss, J. A.; Wirsching, P.; Matsushita, M.; Janda, K. D., Fluorescent Cocaine Probes: A Tool for the Selection and Engineering of Therapeutic Antibodies. *Journal of the American Chemical Society* 2005, 127 (8), 2477-2484.
3. Drash, W.; Blau, M., CNN Front Page News—In America's drug death capital: How heroin is scarring the next generation (cnn.com/2016/09/16/health/huntington-heroin/index.html). 5:45 PM ET, Fri., Sep. 16, 2016 (last seen: December 2017).
4. USDOJ, CD No. 2 ("1. Chasing the Dragon; 2. Heroin Hurts; 3. Heroin is Hell; 4. Heroin is Here; 5 Heroin's Hold"), distributed to the invited attendees of US Attorney—General Loretta E. Lynch's "National Heroin & Opioid Awareness Week" policy speech at College of Pharmacy, University of Kentucky on Sep. 20, 2016. 2016.
5. Kim, K.; Yao, J.; Jin, Z.; Zheng, F.; Zhan, C.-G., Kinetic characterization of cholinesterases and a therapeutically valuable cocaine hydrolase for their catalytic activities against heroin and its metabolite 6-monoacetylmorphine. *Chem. Biol. Interact.* 2018, 293, 107-114.
6. Zhang, T.; Zheng, X.; Kim, K.; Zheng, F.; Zhan, C.-G., Blocking drug activation as a therapeutic strategy to attenuate acute toxicity and physiological effects of heroin. *Sci. Rep.* 2018, 8, 16762. doi: 10.1038/s41598-018-35196-8.
7. Inturrisi, C. E.; Schultz, M.; Shin, S.; Umans, J. G.; Angel, L.; Smon, E. J., Evidence from opiate binding studies that heroin acts through its metabolites. *Life Sci.* 1983, 33(Suppl. 1), 773-776.
8. Strandberg, J. J.; Kugelberg, F. C.; Alkass, K.; Gustaysson, A.; Zahlsen, K.; Spigset, O.; Druid, H., Toxicological analysis in rats subjected to heroin and morphine overdose. *Toxicol. Lett.* 2006, 166, 11-18.
9. Qiao, Y; Han, K.; Zhan, C.-G., Reaction pathways and free energy profiles for cholinesterase-catalyzed hydrolysis of 6-monoacetylmorphine. *Org. Biomol. Chem.* 2014, 12, 2214-2227 (Cover Article).
10. Qiao, Y; Han, K. L.; Zhan, C.-G., Fundamental reaction pathway and free energy profile for butyrylcholinesterase-catalyzed hydrolysis of heroin. *Biochemistry* 2013, 52, 6467-6479.
11. Selley, D. E.; Cao, C. C.; Sexton, T.; Schwegel, J. A.; Martin, T. J.; Childers, S. R., mu-Opioid receptor-mediated G-protein activation by heroin metabolites: evidence for greater efficacy of 6-monoacetylmorphine compared with morphine. *Biochem. Pharmacol.* 2001, 62, 447-455.
12. Wikipedia, en.wikipedia.org/wiki/Morphine#cite note-urlDrugFacts: Heroin_.7C_National_Institute_on_Drug_Abuse_. 28NIDA.29-23 (accessed: Mar. 6, 2018). 2018.
13. NIDA, DrugFacts: Heroin (drugabuse.gov/publications/drugfacts/heroin). 2015.

14. Boix, F.; Andersen, J. M.; Mørland, J., Pharmacokinetic modeling of subcutaneous heroin and its metabolites in blood and brain of mice. *Addict. Biol.* 2013, 18, 1-7.
15. Eddy, N. B.; Howes, H. A., Studies of morphine, codeine and their derivatives VIII Monoacetyl- and diacetylmorphine their hydrogenated derivatives. *J Pharmacol. Exp. Ther.* 1935, 53 (4), 430-439.
16. Wright, C. I.; Barbour, F. A., The respiratory effects of morphine, codeine and related substances IV. The effect of alpha-monoacetylmorphine, monoacetyldihydromorphine, diacetylmorphine (heroin) and diacetyldihydromorphine on the respiratory activity of the rabbit. *J. Pharmacol. Exp. Ther.* 1935, 54 (1), 25-33.
17. Lockridge, O.; Mottershaw-Jackson, N.; Eckerson, H. W.; La Du, B. N., Hydrolysis of diacetylmorphine (heroin) by human serum cholinesterase. *J Pharmacol. Exp. Ther.* 1980, 215 (1), 1-8.
18. Andersen, J. M.; Ripel, A.; Boix, F.; Normann, P. T.; Morland, J., Increased locomotor activity induced by heroin in mice: pharmacokinetic demonstration of heroin acting as a prodrug for the mediator 6-monoacetylmorphine in vivo. *J Pharmacol Exp Ther* 2009, 331 (1), 153-61.
19. Krieter, P.; Chiang, N.; Gyaw, S.; Skolnick, P.; Crystal, R.; Keegan, F.; Aker, J.; Beck, M.; Harris, J., Pharmacokinetic Properties and Human Use Characteristics of an FDA-Approved Intranasal Naloxone Product for the Treatment of Opioid Overdose. *J Clin. Pharmacol.* 2016, 56, 1243-1253.
20. Zaaijer, E. R.; Goudriaan, A. E.; Koeter, M. W.; Booij, J.; van den Brink, W., Acceptability of Extended-Release Naltrexone by Heroin-Dependent Patients and Addiction Treatment Providers in the Netherlands. *Subst. Use Misuse* 2016, 51, 1905-1911.
21. Ritter, A. J., Naltrexone in the treatment of heroin dependence: relationship with depression and risk of overdose. *Australian and New Zealand Journal of Psychiatry* 2002, 36, 224-228.
22. SAMHSA, The Facts about Naltrexone for Treatment of Opioid Addiction (store.samhsa.gov/shin/content//SMA12-4444/SMA12-4444.pdf), HHS Publication No. (SMA) I2-4444. 2012.
23. Gibson, A.; Degenhardt, L., Mortality related to naltrexone in the treatment of opioid dependence: A comparative analysis (ndarc.med.unsw.edu.au/resource/mortality-related-naltrexone-treatment-opioid-dependence-comparative-analysis). *NDARC Technical Report No.* 229 2005.
24. Hwang, C. S.; Janda, K. D., A Vision for Vaccines: Combating the Opioid Epidemic. *Biochemistry* 2017, 56, 5625-5627.
25. Miller III, A.; Glasel, J. A., Comparative Sequence and Immunochemical Analyses of Murine Monoclonal Antimorphine Antibodies. *J Mol. Biol.* 1989, 209, 763-778.
26. Kussie, P. H.; Anchin, J. M.; Subramaniam, S.; Glasel, J. A.; Linthicum, D. S., Analysis of the binding site architecture of monoclonal antibodies to morphine by using competitive ligand binding and molecular modeling. *J Immunol.* 146, 4248-4257.
27. Sawada, J.-I.; Yamazaki, T.; Terao, T., Molecular and biochemical analyses of combining sites of monoclonal anti-morphine antibodies. *Mol. Immunol.* 1993, 30, 77-86.
28. Rahbarizadeh, F.; Rasaee, M. J.; Madani, R.; Rahbarizadeh, M. H.; Omidfar, K., Preparation and Characterization of Specific and High-Affinity Monoclonal Antibodies Against Morphine. *HYBRIDOMA* 2000, 19, 413-417.
29. Yang, T. B.; Zhong, P.; Nie, J. L.; Li, J. S.; Qu, L. N.; Li, Y H.; Kan, G. H., Preparation and Identification of Specific and High-Affinity Monoclonal Antibodies against Morphine. 2002, 21, 197-201.
30. Matsukizono, M.; Kamegawa, M.; Tanaka, K.; Kohra, S.; Arizono, K.; Hamazoe, Y; Sugimura, K., Characterization of a Single Chain Fv Antibody that Reacts with Free Morphine. *Antibodies* 2013, 2, 93-112.
31. Bogen, I. L.; Boix, F.; Nerem, E.; Morland, J.; Andersen, J. M., A Monoclonal Antibody Specific for 6-Monoacetylmorphine Reduces Acute Heroin Effects in Mice. *J Pharmacol. Exp. Ther.* 2014, 349, 568-576.
32. Kvello, A. M. S.; Andersen, J. M.; Oiestad, E. L.; Morland, J.; Bogen, I. L., Pharmacological Effects of a Monoclonal Antibody against 6-Monoacetylmorphine upon Heroin-Induced Locomotor Activity and Pharmacokinetics in Mice. *J Pharmacol. Exp. Ther.* 2016, 358, 181-189.
33. Moghaddam, A.; Borgen, T.; Stacy, J.; Kausmally, L.; Simonsen, B.; Marvik, O. J.; Brekke, O. H.; Braunagel, M., Identification of scFv antibody fragments that specifically recognise the heroin metabolite 6-monoacetylmorphine but not morphine. *J. Immunol. Methods* 2003, 280, 139-155.
34. Pozharski, E.; Wilson, M. A.; Hewagama, A.; Shanafelt, A. B.; Petsko, G.; Ringe, D., Anchoring a Cationic Ligand: The Structure of the Fab Fragment of the Antimorphine Antibody 9B1 and its Complex with Morphine. *Journal of Molecular Biology* 2004, 337 (3), 691-697.
35. Treweek, J. B.; Janda, K. D., An Antidote for Acute Cocaine Toxicity. *Mol. Pharm.* 2012, 9, 969-978.
36. Pozharski, E.; Wilson, M. A.; Hewagama, A.; Shanafelt, A. B.; Petsko, G.; Ringe, D., Anchoring a Cationic Ligand: The Structure of the Fab Fragment of the Antimorphine Antibody 9B1 and its Complex with Morphine. *J. Mol. Biol.* 2004, 337, 691-697.
37. Tiller, K. E.; Tessier, P. M., Advances in Antibody Design. *Annu. Rev. Biomed. Eng.* 2015, 17, 191-216.
38. Giudicelli, V; Duroux, P.; Ginestoux, C.; Folch, G.; Jabado-Michaloud, J.; Chaume, D.; Lefranc, M. P., IMGT/LIGM-DB, the IMGT comprehensive database of immunoglobulin and T cell receptor nucleotide sequences. *Nucleic acids research* 2006, 34 (Database issue), D781-4.
39. Lepore, R.; Olimpieri, P. P.; Messih, M. A.; Tramontano, A., PIGSPro: prediction of immunoGlobulin structures v2. *Nucleic Acid. Res.* 2017, 45 (W1), W17-W23.
40. Maier, J. A.; Martinez, C.; Kasavajhala, K.; Wickstrom, L.; Hauser, K. E.; Simmerling, C., ff14SB: Improving the Accuracy of Protein Side Chain and Backbone Parameters from ff99SB. *Journal of chemical theory and computation* 2015, 11 (8), 3696-3713.
41. D. A. Case; I. Y. Ben-Shalom; S. R. Brozell; D. S. Cerutti; T. E. Cheatham; V. W. D. Cruzeiro; Darden, T. A. *AMBER* 2018, University of California: San Francisco, 2018.
42. Delano, W. L. *The PyMOL Molecular Graphics System, Version* 1.7; Schrödinger, LLC.: 2014.
43. Trott, O.; Olson, A. J., AutoDock Vina: improving the speed and accuracy of docking with a new scoring function, efficient optimization, and multithreading. *Journal of computational chemistry* 2010, 31 (2), 455-461.
44. Wang, J.; Wolf, R. M.; Caldwell, J. W.; Kollman, P. A.; Case, D. A., Development and testing of a general amber force field. *Journal of Computational Chemistry* 2004, 25 (9), 1157-1174.

45. Ryckaert, J.-P.; Ciccotti, G.; Berendsen, H. J. C., Numerical integration of the cartesian equations of motion of a system with constraints: molecular dynamics of n-alkanes. *J. Comput. Phys.* 1977, 23 (3), 327-341.
46. Essmann, U.; Perera, L.; Berkowitz, M. L.; Darden, T.; Lee, H.; Pedersen, L. G., A smooth particle mesh Ewald method. *J. Chem. Phys.* 1995, 103 (19), 8577-93.
47. Robert, X.; Gouet, P., Deciphering key features in protein structures with the new ENDscript server. *Nucleic Acid. Res.* 2014, 42 (W1), W320-W324.
48. Mark, P.; Nilsson, L., Structure and Dynamics of the TIP3P, SPC, and SPC/E Water Models at 298 K. *The Journal of Physical Chemistry A* 2001, 105 (43), 9954-9960.
49. Loncharich, R.; Brooks, B.; Pastor, R., Langevin dynamics of peptides: the frictional dependence of isomerization rates of N-acetylalanyl-N'-methyl amide. *Biopolymers* 1992, 32 (5), 523-35.
50. Madeira, F.; Park, Y M.; Lee, J.; Buso, N.; Gur, T.; Madhusoodanan, N.; Basutkar, P.; Tivey, A. R. N.; Potter, S. C.; Finn, R. D.; Lopez, R., The EMBL-EBI search and sequence analysis tools APIs in 2019. *Nucleic Acid. Res.* 2019.
51. Chin, J. X.; Chung, B. K.-S.; Lee, D.-Y., Codon Optimization OnLine (COOL): a web-based multi-objective optimization platform for synthetic gene design. *Bioinformatics* 2014, 30 (15), 2210-2212.
52. Chen, X.; Xue, L.; Hou, S.; Jin, Z.; Zhang, T.; Zheng, F.; Zhan, C.-G., Long-acting cocaine hydrolase for addiction therapy. *Proc. Natl. Acad. Sci. USA* 2016, 113, 422-427.
53. Chen, X.; Deng, J.; Zheng, X.; Zhang, J.; Zhou, Z.; Wei, H.; Zhan, C.-G.; Zheng, F., Development of a long-acting Fc-fused cocaine hydrolase with improved yield of protein expression. *Chem. Biol. Interact.* 2019, 306, 89-95.
54. Chen, X.; Cui, W.; Deng, J.; Hou, S.; Zhang, J.; Ding, X.; Zheng, X.; Wei, H.; Zhou, Z.; Kim, K.; Zhan, C.-G.; Zheng, F., Development of Fc-fused Cocaine Hydrolase for Cocaine Addiction: Catalytic and Pharmacokinetic Properties. *AAPS J* 2018, 20, 53. doi: 10.1208/s12248-018-0214-9.
55. Nelson, A. L.; Dhimolea, E.; Reichert, J. M., Development trends for human monoclonal antibody therapeutics. *Nature Reviews Drug Discovery* 2010, 9 (10), 767-774.
56. Jun-ichi, S.; Takeshi, Y; Tadao, T., Molecular and biochemical analyses of combining sites of monoclonal anti-morphine antibodies. *Molecular Immunology* 1993, 30 (1), 77-86.
57. Glasel, J. A.; Braudbury, W. M.; Venn, R. F., Properties of murine anti-morphine antibodies. *Molecular Immunology* 1983, 20 (12), 1419-1422.
58. Pozharski, E.; Wilson, M. A.; Hewagama, A.; Shanafelt, A. B.; Petsko, G.; Ringe, D., Anchoring a Cationic Ligand: The Structure of the Fab Fragment of the Anti-morphine Antibody 9B1 and its Complex with Morphine. *Journal of Molecular Biology* 2004, 337 (3), 691-697.
59. Kussie, P. H.; Anchin, J. M.; Subramaniam, S.; Glasel, J. A.; Linthicum, D. S., Analysis of the binding site architecture of monoclonal antibodies to morphine by using competitive ligand binding and molecular modeling. *Journal of immunology* (Baltimore, Md.: 1950) 1991, 146 (12), 4248-57.
60. Moghaddam, A.; Borgen, T.; Stacy, J.; Kausmally, L.; Simonsen, B.; Marvik, O. J.; Brekke, O. H.; Braunagel, M., Identification of scFv antibody fragments that specifically recognise the heroin metabolite 6-monoacetylmorphine but not morphine. *Journal of Immunological Methods* 2003, 280 (1), 139-155.
61. Matsukizono, M.; Kamegawa, M.; Tanaka, K.; Kohra, S.; Arizono, K.; Hamazoe, Y.; Sugimura, K., Characterization of a Single Chain Fv Antibody that Reacts with Free Morphine. *Antibodies* 2013, 2 (1), 93-112.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An antigen-binding fragment of an isolated antibody that selectively binds one or more of 6-MAM, morphine, heroin, hydrocodone, oxycodone, meperidine, and fentanyl, and does not selectively bind naloxone or naltrexone, the antigen-binding fragment of the isolated antibody comprising:
- a first complementarity determining region of a heavy chain of the isolated antibody, with the first complementarity determining region of the heavy chain comprising SEQ ID NO: 65, 66, or 67;
- a second complementarity determining region of the heavy chain of the isolated antibody, with the second complementarity determining region of the heavy chain comprising SEQ ID NO: 68, 69, or 70;
- a third complementarity determining region of the heavy chain of the isolated antibody, with the third complementarity determining region of the heavy chain comprising SEQ ID NO: 68, 69, or 70;
- a first complementarity determining region of a light chain of the isolated antibody, with the first complementarity determining region of the light chain comprising SEQ ID NO: 71 or 72;
- a second complementarity determining region of the light chain of the isolated antibody, with the second complementarity determining region of the light chain comprising GTN, STN, or DTS; and
- a third complementarity determining region of the light chain of the isolated antibody, with the third complementarity determining region of the light chain comprising SEQ ID NO: 73, 74, or 75.

2. The antigen-binding fragment of claim 1, wherein
the first complementarity determining region of the heavy chain comprises SEQ ID NO: 65,
the second and third complementarity determining region of the heavy chain comprises SEQ ID NO: 68,
the first complementarity determining region of the light chain comprises SEQ ID NO: 71, the second complementarity determining region of the light chain comprises GTN, and the third complementarity determining region of the light chain comprises SEQ ID NO: 73.

3. The antigen-binding fragment of claim 1, wherein the first complementarity determining region of the heavy chain comprises SEQ ID NO: 66, the second and third complementarity determining region of the heavy chain comprises SEQ ID NO: 69, the first complementarity determining region of the light chain comprises SEQ ID NO: 71, the second complementarity determining region of the light chain comprises STN, and the third complementarity determining region of the light chain comprises SEQ ID NO: 74.

4. The antigen-binding fragment of claim 1, wherein the first complementarity determining region of the heavy chain comprises SEQ ID NO: 67, the second and third complementarity determining region of the heavy chain comprises SEQ ID NO: 70, the first complementarity determining region of the light chain comprises SEQ ID NO: 72, the second complementarity determining region of the light chain comprises DTS, and the third complementarity determining region of the light chain comprises SEQ ID NO: 75.

5. An isolated antibody that selectively binds one or more of 6-MAM, morphine, heroin, hydrocodone, oxycodone, meperidine, and fentanyl, and does not selectively bind naloxone or naltrexone, wherein the antibody is selected from the group consisting of:

(i) an antibody comprising SEQ ID NO: 5;
(ii) an antibody comprising SEQ ID NO: 12;
(iii) an antibody comprising SEQ ID NOs: 5 and 12;
(iv) an antibody comprising SEQ ID NO: 25;
(v) an antibody comprising SEQ ID NO: 51;
(vi) an antibody comprising SEQ ID NOs: 25 and 51;
(vii) an antibody comprising (a) SEQ ID NO: 72, (b) GTN, STN, or DTS, and (c) SEQ ID NO: 73, 74, or 75; and
(viii) an antibody comprising (a) SEQ ID NO: 65, 66, or 67, (b) SEQ ID NO: 68, 69, or 70, (c) SEQ ID NO: 71 or 72, (d) GTN, STN, or DTS, and (e) SEQ ID NO: 73, 74, or 75.

6. The isolated antibody of claim 5, wherein the antibody comprises SEQ ID NOs: 5 and 12.

7. The isolated antibody of claim 6, wherein the antibody has a binding affinity of 127 $K_d$ (nM) or less with heroin, 6-MAM, and morphine.

8. The isolated antibody of claim 6, wherein the antibody has a binding affinity of 12 $K_d$ (nM) or less with heroin and 6-MAM.

9. The isolated antibody of claim 6, wherein the antibody has a binding affinity of more than 10,000 $K_d$ (nM) with naloxone and naltrexone.

10. The isolated antibody of claim 5, wherein the antibody comprises SEQ ID NOs: 25 and 51.

11. The isolated antibody of claim 5, wherein the antibody comprises SEQ ID NOs: 66, 69, 71, STN, and 74.

12. The isolated antibody of claim 5, wherein the antibody comprises SEQ ID NOS: 67, 70, 72, DTS, and 75.

* * * * *